United States Patent

Frasca, Jr.

[11] Patent Number: 6,055,506
[45] Date of Patent: Apr. 25, 2000

[54] OUTPATIENT CARE DATA SYSTEM

[75] Inventor: Ralph V. Frasca, Jr., Palm Harbor, Fla.

[73] Assignee: Unitron Medical Communications, Inc., Clearwater, Fla.

[21] Appl. No.: 08/845,318

[22] Filed: Apr. 25, 1997

[51] Int. Cl.[7] ..................................... G06F 17/60
[52] U.S. Cl. ................... 705/3; 705/2; 604/66; 604/67
[58] Field of Search ................... 705/1, 2, 3, 8, 705/9, 22; 604/66, 67; 700/99, 100

[56] References Cited

U.S. PATENT DOCUMENTS

| | | | |
|---|---|---|---|
| 3,872,448 | 3/1975 | Mitchell, Jr. | 705/3 |
| 4,531,527 | 7/1985 | Reinhold, Jr. et al. | 600/509 |
| 4,737,912 | 4/1988 | Ichikawa | 364/413 |
| 4,803,625 | 2/1989 | Fu et al. | 600/483 |
| 4,878,175 | 10/1989 | Norden-Paul et al. | 705/2 |
| 4,933,873 | 6/1990 | Kaufman et al. | 364/513.5 |
| 5,012,229 | 4/1991 | Lennon et al. | 340/706 |
| 5,036,462 | 7/1991 | Kaufman et al. | 364/413.01 |
| 5,038,800 | 8/1991 | Oba | 128/904 |
| 5,065,315 | 11/1991 | Garcia | 705/2 |
| 5,084,828 | 1/1992 | Kaufman et al. | 364/479 |
| 5,265,010 | 11/1993 | Evans-Paganelli et al. | 364/413.02 |
| 5,291,399 | 3/1994 | Chaco | 705/3 |
| 5,319,363 | 6/1994 | Welch et al. | 340/825.36 |
| 5,319,543 | 6/1994 | Wilhelm | 364/401 |
| 5,361,202 | 11/1994 | Doue | 705/3 |
| 5,410,471 | 4/1995 | Alyfuku et al. | 364/413.02 |
| 5,549,117 | 8/1996 | Tacklind et al. | 600/529 |
| 5,558,638 | 9/1996 | Evers et al. | 604/66 |
| 5,713,350 | 2/1998 | Yokota et al. | 600/300 |
| 5,724,580 | 3/1998 | Levin et al. | 707/104 |
| 5,845,253 | 12/1998 | Rensimer et al. | 705/2 |
| 5,867,821 | 2/1999 | Ballantyne et al. | 705/2 |

FOREIGN PATENT DOCUMENTS

| | | | |
|---|---|---|---|
| 233731 | 9/1993 | Japan | C06F 15/42 |
| 22495 | 1/1997 | Japan | C08B 25/04 |

OTHER PUBLICATIONS

"Current Status of Telemedicine–Medical Circumstances Being Changed by Network", Journal of Media, vol. 13, No. 10, p. 9–11, Oct. 1995.

Helen Ellis Memorial Hospital, Tampa Bay Area Hospital and Telemedicine Firm Join to Launch Moon—A Medical Communications Network Which Brings the Hospital into the Patient's Home, Dialog File 613:Pr Newswire, pp. 1–2, Oct. 1995.

LanVision Systems, Inc., Health Information System Chooses LanVision as its Document Imaging Partner, Dialog File 613:PR Newswire, pp. 1–2, Mar. 1997.

*Primary Examiner*—Emanuel Todd Voeltz
*Assistant Examiner*—John W. Hayes
*Attorney, Agent, or Firm*—Marshall, O'Toole, Gerstein, Murray & Borun

[57] ABSTRACT

An outpatient care data system dedicated to the transmission, storage and retrieval of outpatient data relating to care of outpatients is provided with a regional data system located at a regional location, a plurality of metropolitan area data systems operatively connected to the regional data system, each of the metropolitan area data systems being located at a different metropolitan location. Each metropolitan area data system may be provided with an electronic nursing station located within a hospital and first and second types of outpatient systems operatively coupled to the electronic nursing station on a real-time basis. The first type of outpatient system is situated at a first non-hospital location remote from the hospital and includes a medical device associated with an outpatient present at the first non-hospital location, and the second type of outpatient system is situated at a second non-hospital location remote from the hospital and includes a medical device associated with an outpatient present at the second non-hospital location.

29 Claims, 15 Drawing Sheets

6,055,506

OUTPATIENT CARE DATA SYSTEM

BACKGROUND OF THE INVENTION

The present invention is directed to an outpatient care data system that tracks the status of patients at locations remote from a hospital.

A hospital typically has a computerized patient data network that keeps track of the medical status of patients currently in the hospital. Such a network could keep track of medical treatments administered to the patients, billing data relating to costs incurred by the patients, medical history data relating to patients such as prior medical procedures received by the patients, medical condition data such as medications to which patients are allergic, etc.

Although generally advantageous to track the medical status of the patients when they are in the hospital, such an in-hospital network cannot keep track of patients after they leave the hospital. For example, when a patient is discharged from the hospital to a skilled care facility, personnel at the skilled care facility must manually obtain the patient's medical and personal information from the patient and/or the hospital, resulting in duplication of effort and the possibility of erroneous information being entered or pertinent information being omitted. This disadvantage is aggravated by the current tendency to minimize a patient's stay in the hospital due to pressures to limit medical costs.

SUMMARY OF THE INVENTION

The present invention is directed to an outpatient care data system dedicated to the transmission, storage and retrieval of outpatient data relating to care of outpatients and to an electronic nursing station adapted to be used in the outpatient care data system.

In one aspect, the outpatient care data system includes a regional data system for a regional area and a plurality of metropolitan area data systems operatively connected to the regional data system. The regional and metropolitan area data systems store outpatient data in the form of a plurality of comprehensive medical records for a plurality of outpatients located within the regional and metropolitan areas. The medical records include, for each outpatient, an identification of the outpatient, an identification of the outpatient's physician, and data representing the medical history of the outpatient.

Each metropolitan area data system may be provided with an electronic nursing station located within a hospital and first and second types of outpatient systems operatively coupled to the electronic nursing station on a real-time basis. The first type of outpatient system is situated at a first non-hospital location remote from the hospital and includes a medical device associated with an outpatient present at the first non-hospital location, and the second type of outpatient system is situated at a second non-hospital location remote from the hospital and includes a medical device associated with an outpatient present at the second non-hospital location.

Each metropolitan area data system may also include a plurality of interactive computer terminals disposed at different terminal locations remote from the hospital at which the electronic nursing station is located. The interactive computer terminals facilitate real-time retrieval of data in the comprehensive medical records for the outpatients.

In a second aspect, the outpatient care data system includes first and second electronic nursing stations located within first and second hospitals, respectively, first and second outpatient systems operatively coupled to the first electronic nursing station on a real-time basis, third and fourth outpatient systems operatively coupled to the second electronic nursing station on a real-time basis, a data storage system operatively coupled to the first and second electronic nursing stations for storing outpatient data received from the first and second electronic nursing stations, and a plurality of interactive computer terminals operatively coupled to the data storage system on a real-time basis.

The data storage system stores outpatient data in the form of a plurality of comprehensive medical records for a plurality of outpatients associated with the first and second electronic nursing stations, the medical records including, for each outpatient, an identification of the outpatient, an identification of the outpatient's physician, and data representing the medical history of the outpatient.

In another aspect, the outpatient care data system includes an electronic nursing station located within a hospital and having a data storage system for storing outpatient data relating to outpatients present at non-hospital locations outside of the hospital, a plurality of interactive data terminals for communicating with the data storage system on a real-time basis, and a monitor for checking outpatient data stored in the data storage system and generating messages relating to the outpatients. The outpatient care data system also includes first and second outpatient systems operatively coupled to the electronic nursing station on a real-time basis. The first outpatient system is situated at a first non-hospital location remote from the hospital and includes a medical device associated with an outpatient present at the first remote location and the second outpatient system is situated at a second non-hospital location remote from the hospital and includes a medical device associated with an outpatient present at the second remote location.

One of the outpatient systems may be a skilled care facility system having at least one medical device for administering medical treatment to an outpatient at a non-hospital location, at least one medical device for sensing a medical condition of an outpatient at a non-hospital location and generating outpatient condition data relating to the medical condition, and means for transmitting the outpatient condition data from the non-hospital location to the electronic nursing station on a real-time basis. One of the outpatient systems may include at least one medical device located at an outpatient home and means for transmitting outpatient data from the outpatient home to the electronic nursing station on a real-time basis.

The invention is also directed to an electronic nursing station adapted to be used as part of an outpatient care data system dedicated to the transmission, storage and retrieval of outpatient data relating to care of outpatients. The electronic nursing station includes a data storage system for storing comprehensive medical data relating to outpatients, a monitor for checking outpatient data stored in the data storage system and generating messages relating to the outpatients, a data receiver adapted to receive outpatient data from first and second outpatient systems situated at first and second locations remote from the electronic nursing station, and a data transmitter for transmitting outpatient data to a plurality of interactive computer terminals disposed at different terminal locations remote from the electronic nursing station on a real-time basis.

The monitor used in the electronic nursing station may include means for determining whether a deliverable medical device was delivered to an outpatient home in accordance with a scheduled delivery time and means for generating a message at the electronic nursing station relating to whether the deliverable medical device was delivered in accordance with the scheduled delivery time.

The monitor could include means for determining whether a medical clinician checked into an outpatient home in accordance with a scheduled check-in time and means for generating a message at the electronic nursing station relating to whether the medical clinician checked in in accordance with the scheduled check-in time. The monitor could include means for determining whether a medical clinician checked out of an outpatient home in accordance with a scheduled check-out time and means for generating a message at the electronic nursing station relating to whether the medical clinician checked out in accordance with the scheduled check-out time. The monitor could also include means for determining the duration of a visit of a medical clinician to an outpatient home and means for generating a message at the electronic nursing station relating to whether the duration of the visit is in accordance with a specified parameter, for example a minimum time.

The monitor could also include means for comparing outpatient data representing a clinical condition of an outpatient with a predetermined limit and means for generating a message at the electronic nursing station relating to whether the outpatient data is within the predetermined limit.

These and other features of the present invention will be apparent to those of ordinary skill in the art in view of the detailed description of the preferred embodiment, which is made with reference to the drawings, a brief description of which is provided below.

DETAILED DESCRIPTION OF A PREFERRED EMBODIMENT

Figure 1:
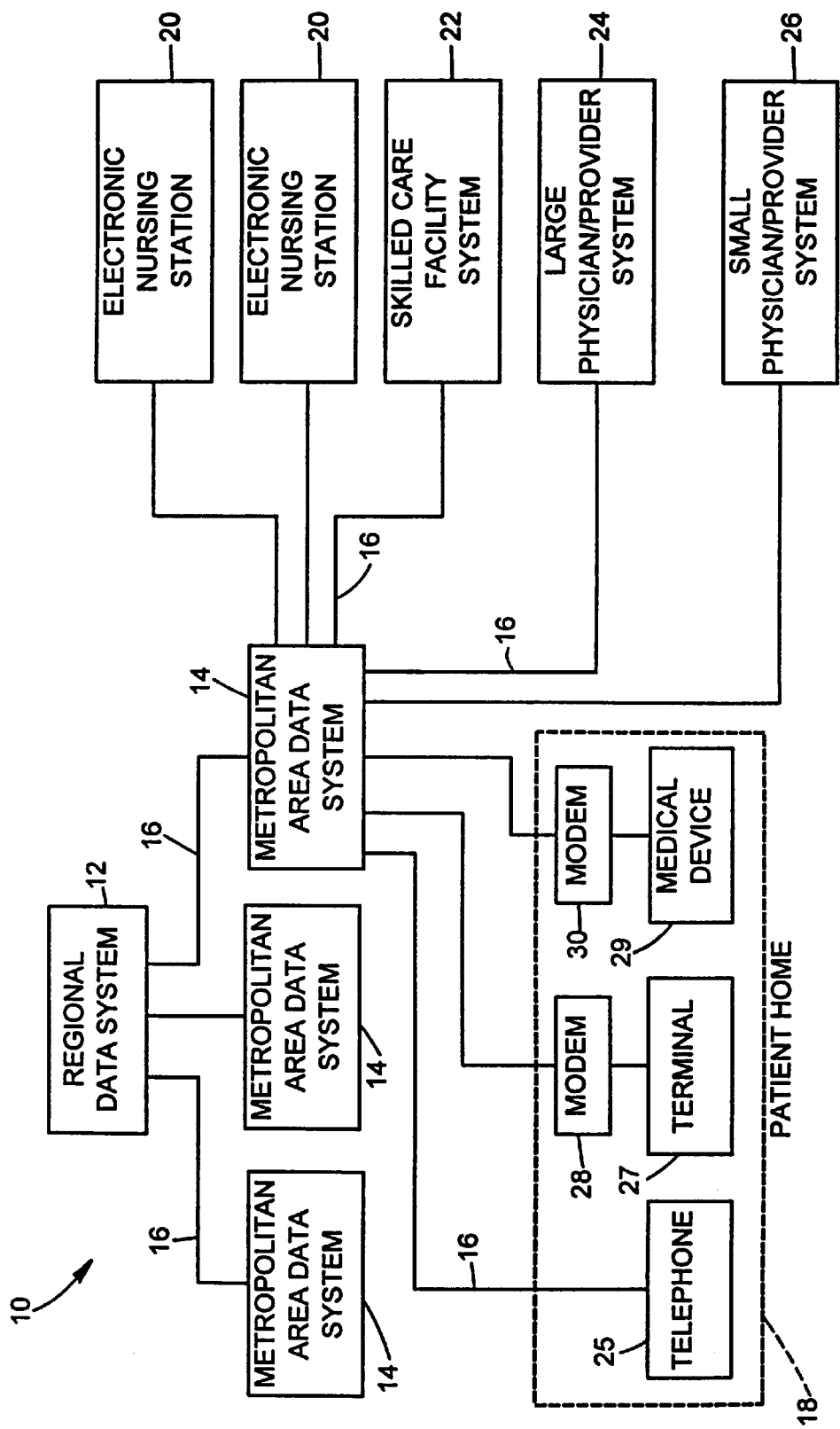
FIG. 1 is a block diagram of a preferred embodiment of an outpatient care data system in accordance with the invention.

FIG. 1 is a block diagram of a preferred embodiment of an outpatient care data system 10 in accordance with the invention. As used herein, the term "outpatient" means a patient present at a location (either fixed or moving) not in a hospital. The outpatient care system 10 has a regional data system 12 operatively connected to a plurality of metropolitan area data systems 14 via one or more data links 16, which data links may be links established through the telephone system or the Internet, for example.

One of the metropolitan area data systems 14 is shown connected to a patient home 18, a plurality of electronic nursing stations 20, a skilled care facility system 22, a large physician/provider system 24 and a small physician/provider system 26 via a plurality of data links 16, which may be the same type of data links as the links 16. Each electronic nursing station 20 within the system 10 would typically be provided at a different hospital. The electronic nursing stations 20 could also be disposed at non-hospital locations where skilled care personnel are present.

Although the rightmost metropolitan area data system 14 in FIG. 1 is shown connected to only one patient home 18 and one each of the systems 22, 24, 26, it should be understood that each metropolitan area data system 14 would typically be connected to a plurality of patient homes 18 and one or more of the systems 22, 24, 26. Alternatively, the metropolitan area data system 14 could be connected to only a subset of the systems 18, 20, 22, 24, 26.

The patient home 18 is shown to include a touch-tone telephone 25, a data terminal 27 connected to the metropolitan area data system 14 via a modem 28, and a medical device 29 connected to the metropolitan area data system 14 via a modem 30. The data terminal 27 may be a CRT terminal or personal computer for entering outpatient data into the system 10 or retrieving outpatient data from the system 10. The medical device 29 may be used to administer a medical treatment to a patient and/or to monitor a clinical condition of the patient, such as the patient's heartbeat, pulse rate, etc.

The devices 25, 27, 29 at the patient home 18, the electronic nursing stations 20, and the systems 22, 24, 26 are operatively connected to the metropolitan area data systems 14 on a real-time basis. As used herein, the term "real-time" means that substantially all data transfers occur within a matter of seconds of the requests pursuant to which such data transfers are made.

Although the block diagram of FIG. 1 is shown in a hierarchical structure to illustrate the operation of the system 10, it should be understood that all of the data links 16 may be established by a common communication medium, such as through the telephone system or the Internet. Also, the outpatient care data system 10 could include multiple regional data systems 12, each of which is connected to a plurality of metropolitan area data systems 14 and their associated devices and systems. The regional data systems 12 could be interconnected via the telephone system or the Internet, for example.

Figure 2:
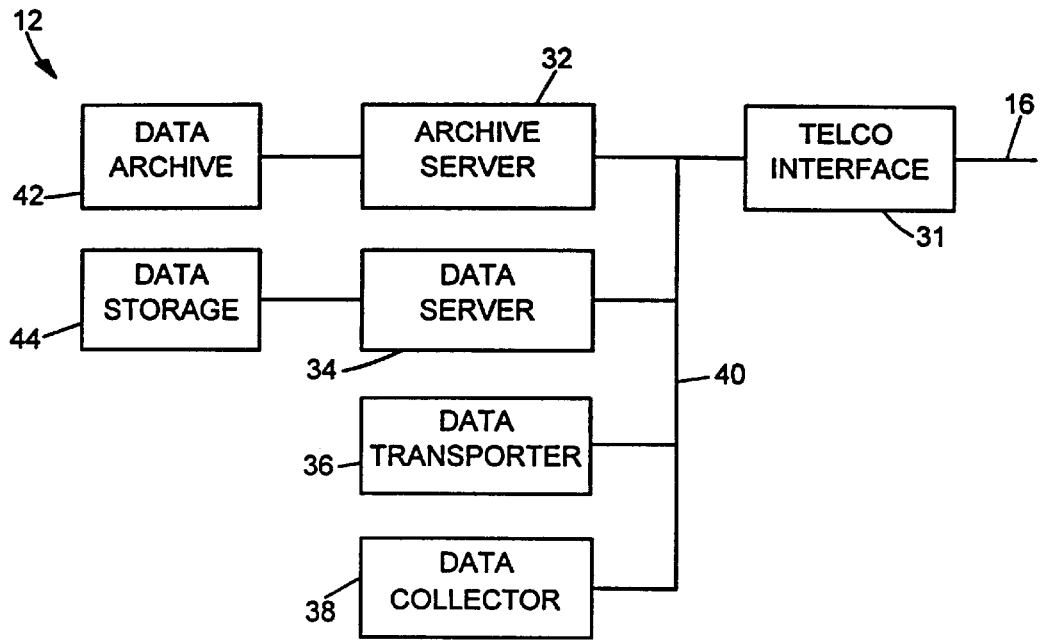
FIG. 2 is a block diagram of the regional data system shown schematically in FIG. 1.

FIG. 2 is a block diagram of the regional data system 12 shown schematically in FIG. 1. Referring to FIG. 2, the regional data system 12 has a conventional interface 31 which facilitates data communication over the telephone system, an archive server 32, a data server 34, a data transporter 36 and a data collector 38, all of which are interconnected via a data link 40.

The archive server 32 is connected to a data archive unit 42 which is used for long-term storage of inactive outpatient data records. The data archive 42 may be a jukebox-type device containing a plurality of writable CD ROMs onto which data may be archived. The data server 34, which could be provided in the form of a conventional SQL relational database server commercially available from Oracle, is connected to a data storage unit 44 which is used for short-term storage of active outpatient data records. The archive server 32 periodically (e.g. every day) checks the outpatient data records stored in the data storage unit 44 and archives all data records which have not been edited or accessed within a predetermined period of time, such as 60 days. All such data records are stored in the data archive unit 42 and deleted from the data storage unit 44. The regional data center 12 is designed to store a duplicate set of all outpatient records generated by the metropolitan area data systems 14 to which it is connected.

The data transporter 36 is used to transmit outpatient data records throughout the system 10 and the data collector 38 is used to receive outpatient data records from various points within the system 10, as described in more detail below. The data transporter 36 and the data collector 38 could be provided in the form of Alpha mini-computers commercially available from Digital Equipment Corporation.

Figure 3:
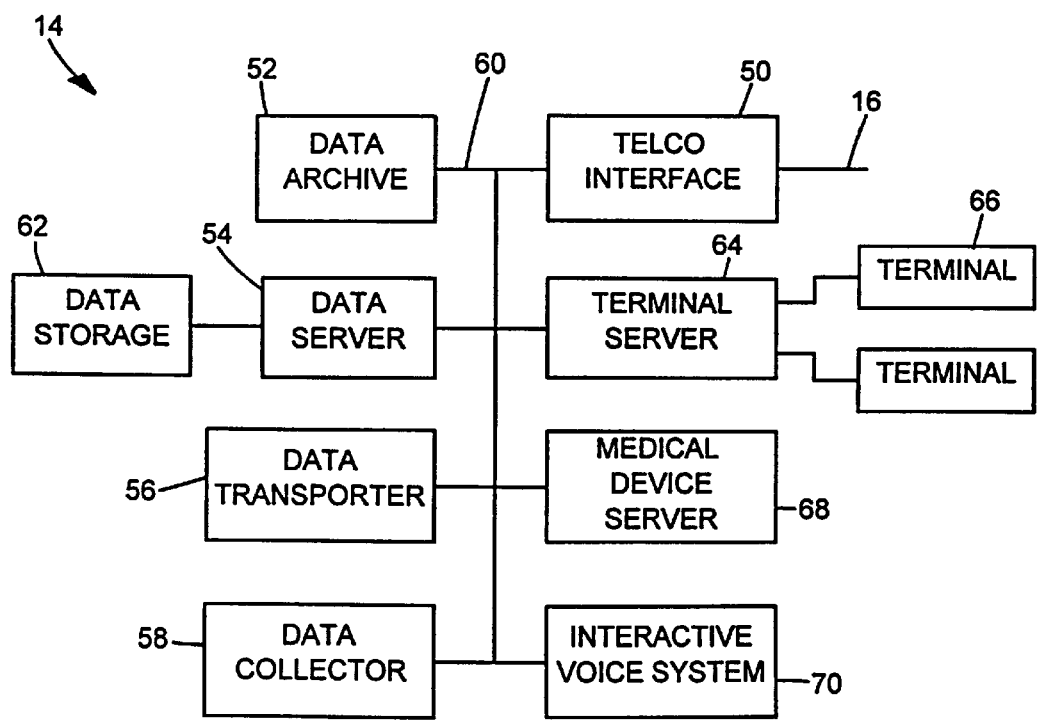
FIG. 3 is a block diagram of one of the metropolitan area data systems shown schematically in FIG. 1.

FIG. 3 is a block diagram of one of the metropolitan area data systems 14 shown schematically in FIG. 1. Referring to FIG. 3, the metropolitan area data system 14 has an interface 50 which facilitates data communication over the telephone system, an archive server 52, a data server 54, a data transporter 56 and a data collector 58, all of which are interconnected via a data channel 60.

The data server 54 is connected to a data storage unit 62 which is used for short-term storage of active outpatient data records. The archive server 52 periodically checks the outpatient data records stored in the data storage unit 62 and causes all data records which have not been edited or accessed within a predetermined period of time to be archived in the data archive unit 42 (FIG. 2) of the regional data system 12 and deleted from the data storage unit 62. The data transporter 56 is used to transmit outpatient data records throughout the system 10, and the data collector 58 is used to receive outpatient data records from various points within the system 10, as described below.

The metropolitan area data system 14 includes a terminal server 64 which is connected to a plurality of interactive data terminals 66 which may be used to enter outpatient data into the system 10 or review outpatient data previously entered into the system 10. The metropolitan area data system 14 also has a medical device server 68 and an interactive voice system 70. The medical device server 68 responds to data transmissions transmitted to the metropolitan area data system 14 via the interface 50 by various medical devices throughout the system 10, which medical devices include, for example, the medical device 29 (FIG. 1) in the patient home 18. The manner in which those data transmissions are processed by the medical device server 68 is described below.

The interactive voice system 70 responds to data transmissions manually transmitted to the metropolitan area data system 14 via the interface 50 by medical personnel, for example, through the use of the touch-tone telephone 25 (FIG. 1). Such transmissions may include vital signs or other physiological patient parameters transmitted by a nurse or clinician from a patient's home.

Although FIG. 2 shows the regional data system 12 as having only one archive server 32, one data server 34, one data transporter 36, and one data collector 38, more than one of each of those components could be used, depending on the size of the system 10. Similar duplication of components could be made in connection with the system shown in FIG. 3.

Figure 4:
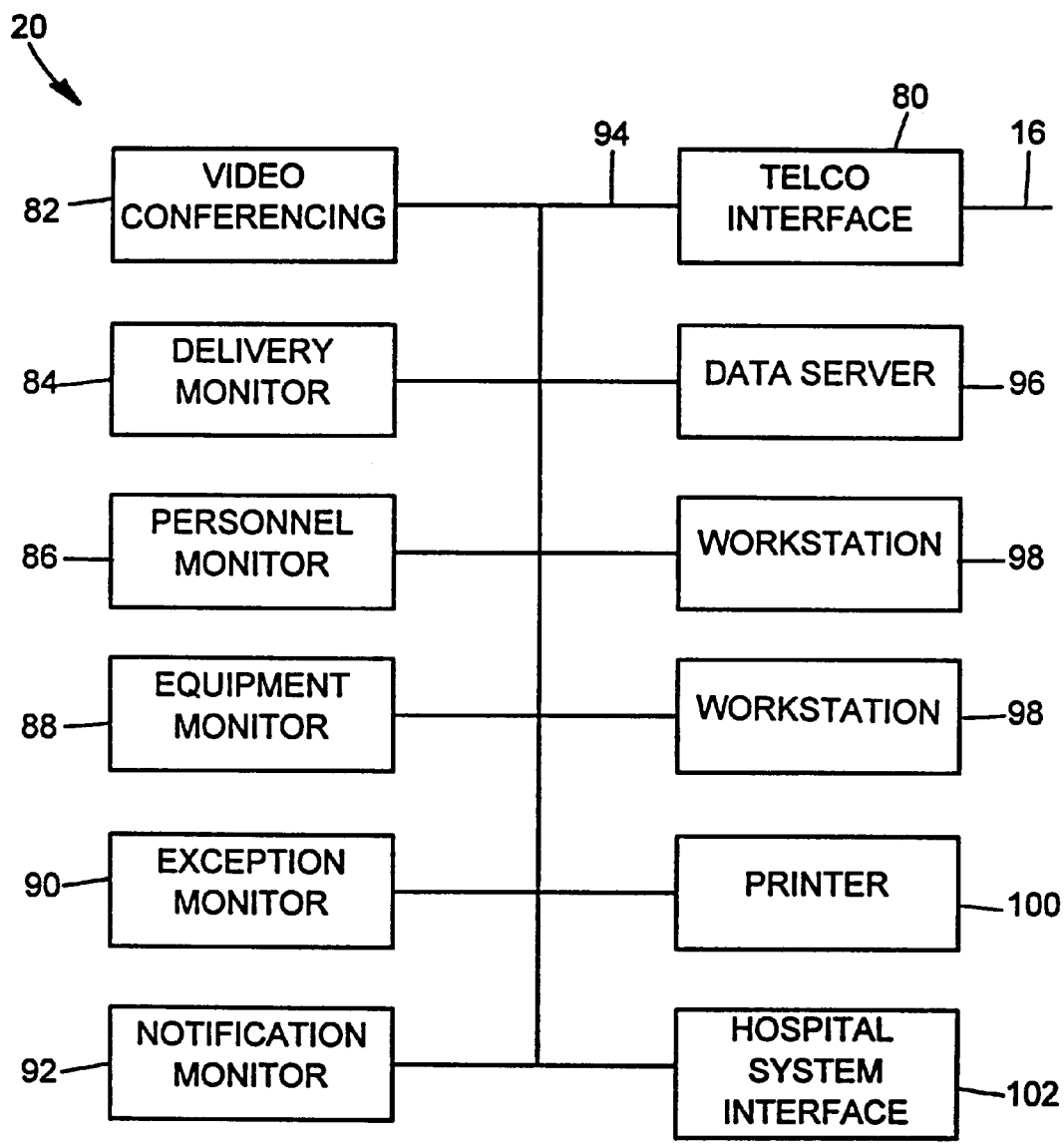
FIG. 4 is a block diagram of one of the electronic nursing stations shown schematically in FIG. 1.

FIG. 4 is a block diagram of one of the electronic nursing stations 20 shown schematically in FIG. 1. The electronic nursing station 20, which is located within a hospital, stores outpatient data records collected from different points within the system 10 but outside the hospital, such as from the patient home 18, from the skilled care facility system 22, or from the physician/provider systems 24, 26. Those outpatient data records, which include data records containing real-time clinical data, are monitored to detect the presence of any conditions that require notification of a doctor or other medical personnel.

Referring to FIG. 4, the electronic nursing station 20 has an interface 80, a video conferencing system 82, a delivery monitor 84, a personnel monitor 86, an equipment monitor 88, an exception monitor 90, and a physician notification monitor 92, all of which are interconnected by a data channel 94. The electronic nursing station 20 also includes a data server 96, a plurality of workstations 98, one or more printers 100, and a hospital system interface 102, all of which are connected to the data channel 94.

The data server 96, which may be a conventional SQL data server commercially available from Oracle, has memory in which outpatient data relating to all the patients associated with that particular electronic nursing station is stored. Although the electronic nursing station 20 is located in the hospital, the patients associated with it would be at geographic locations other than the hospital, including patients' homes, remote skilled care facilities, and physician/provider offices. The workstations 98 may be used to enter outpatient data records into the data server 96 or to view outpatient data already stored in the data server 96.

The hospital at which the electronic nursing station 20 is located would typically have its own data processing system which tracks the status of patients located within the hospital. The hospital system interface 102, which is optional, is used to interface with hospital's data processing system so that patient data may be transferred between the two systems.

The monitors 84, 86, 88, 90, 92, in combination with the data server 96 in which the outpatient data is stored, are used to check for the presence of conditions, such as patient vital signs indicating a dangerous medical condition, which require human interaction or physician notification. Each of the monitors 84, 86, 88, 92 has a display device, such as a CRT, on which attention or alarm messages can be displayed. As described below, in response to detecting such conditions, appropriate messages are displayed on the display devices of the monitors.

Figure 5:
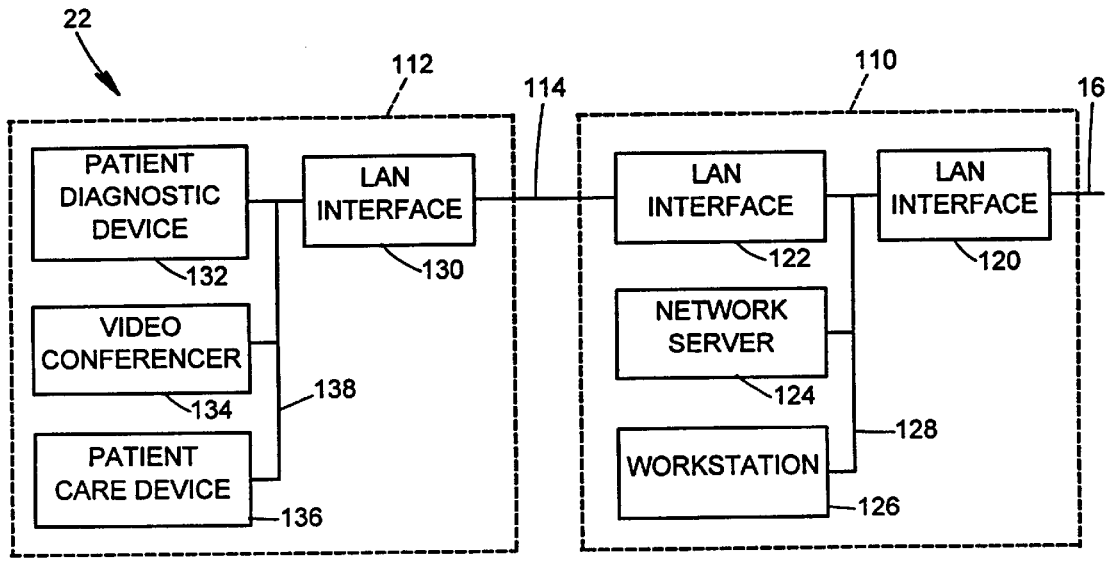
FIG. 5 is a block diagram of the skilled care facility system shown schematically in FIG. 1.

FIG. 5 is a block diagram of the skilled care facility system 22 shown schematically in FIG. 1. The skilled care facility system 22 is situated in a skilled care facility, such as a nursing home, a transitional care unit, or a skilled nursing facility, located at a geographic location different from the locations of the other components of the system 10. Referring to FIG. 5, the skilled care facility system 22, which may be in the form of a local area network (LAN), is composed of a data center 110 and a plurality of remote medical units 112, one of which is shown in FIG. 5. The data center 110 may be connected to each of the remote medical units 112 via a data link 114, which may be a wireless data link or a physical link accomplished with an RJ-45 connector.

The data center 110 may be provided with an interface 120 to the telephone system, a LAN interface 122, a network server 124, such as a multi-processor personal computer, one or more workstations 126, all of which are interconnected via a data link 128. The medical unit 112 is shown to include a LAN interface 130, a patient diagnostic device 132, a video conferencer 134, and a patient care device 136, all of which are interconnected via a data link 138.

The patient diagnostic device 132, such as a heart rate monitor, is used to monitor a patient and periodically transmits data relating to the condition being monitored to the data center 110. That data is stored locally in memory in the network server 124 and is also immediately transmitted to the metropolitan area data system 14 to which the skilled care facility system 22 is connected. The workstation 126 may be used to enter outpatient data into or view outpatient data stored in the memory of the network server 124. The patient care device 136, which may be a ventilator for example, may periodically transmit data relating to its operational status to the data center 110, which data is stored locally in the network server 124 and immediately transmitted to the metropolitan area data system 14 for storage.

Figure 6:
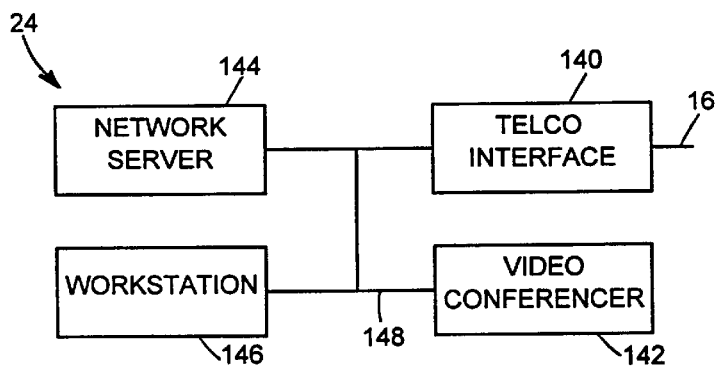
FIG. 6 is a block diagram of the large physician/provider system shown schematically in FIG. 1.

FIG. 6 is a block diagram of the large physician/provider system 24 shown schematically in FIG. 1. The system 24 is situated within a relatively large doctor or provider office located at a distinct geographic location remote from the metropolitan area data system 14. Referring to FIG. 6, the system 24 may include an interface 140 to the telephone system, a video conferencer 142, a network server 144, and one or more workstations 146, all of which are interconnected via a data link 148. The workstation 146 may be used to enter data relating to the patients visiting the physician/provider office at which the system 24 is located or viewing data relating to those patients. The outpatient data that is entered into the memory of the network server 144 is also immediately transmitted to the metropolitan area data system 14 to which the system 24 is connected for storage.

Figure 7:
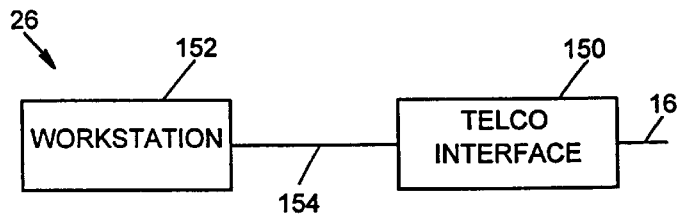
FIG. 7 is a block diagram of the small physician/provider system shown schematically in FIG. 1.

FIG. 7 is a block diagram of the small physician/provider system 26 shown schematically in FIG. 1. The system 26 is situated within a relatively small doctor or provider office located at a distinct geographic location remote from the metropolitan area data system 14. Referring to FIG. 7, the system 26 is shown to include an interface 150 to the telephone system and a workstation 152 interconnected via a data link 154. The workstation 152 may be used to enter data relating to the patients visiting the physician/provider office at which the system 22 is located or viewing data relating to those patients. Any outpatient data that is entered into the memory of the workstation 152 is also immediately transmitted to the metropolitan area data system 14 to which the system 26 is connected for storage.

Outpatient Data

Figure 8:
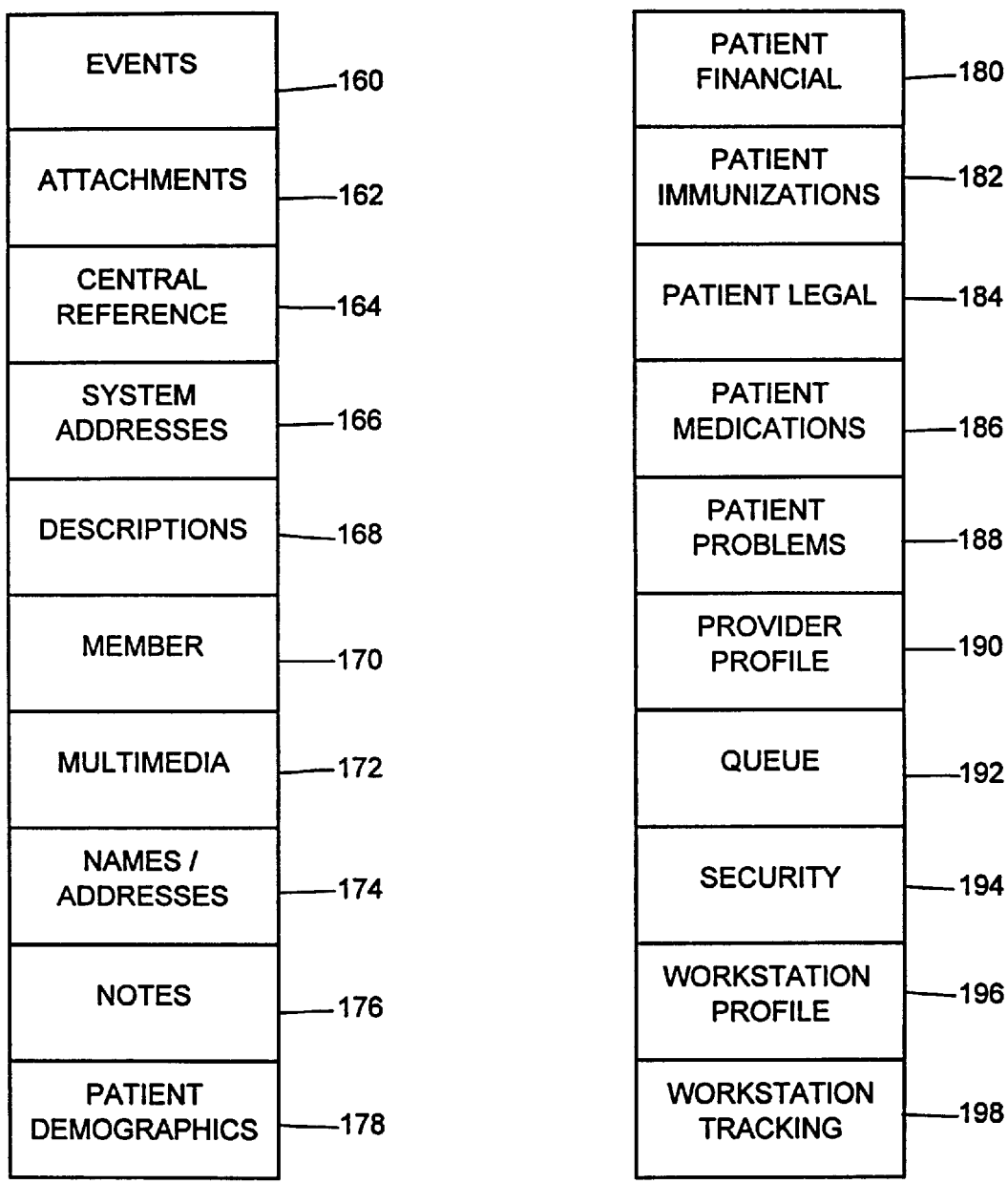
FIG. 8 illustrates a number of data tables that are used during operation of the outpatient care data system.

FIG. 8 illustrates a number of data tables that are stored at the various systems described above. Each data table contains numerous individual data records. The individual data records are distributed throughout the system 10 in a hierarchical manner in that the regional data system 12 contains (in either data archive unit 42 or data storage unit 44 shown in FIG. 2) all of the data records generated by the systems and devices directly or indirectly connected to the regional data system 12 and in that each metropolitan area data system 14 contains all of the data records generated by the systems and devices connected to it. Thus, each metropolitan area data system 14 will store a unique set of data records, and the regional data system 12 will store each of those sets of data records.

The outpatient data is stored in various locations of the system 10 in the form of comprehensive medical records for the outpatients associated with the system 10, the medical record for each patient (comprising numerous individual data records for each patient) being analogous to a complete medical chart of the patient that would be used by a hospital. As described below, the medical record for each patient includes an identification of the patient, the address of the patient, an identification of the patient's physician, and data representing the medical history of the patient.

Referring to FIG. 8, the outpatient data includes an events table 160 that stores various types of outpatient data, such as data relating to clinical patient conditions generated by patient diagnostic devices, the status of patient care devices, patient medical data, etc. An attachments table 162 is used to store additional data relating the events represented in the events table 160. A central reference table 164 includes, for each patient, the interested parties connected to the system 10 to which data regarding that patient should be sent. A system addresses table 166 contains the electronic system addresses of the interested parties set forth in the central reference table 164 (the interested parties will typically include at least one electronic nursing station). A descriptions table 168 contains data which is used in the generation of various screen displays in the system 10.

A member table 170 stores an identification of all the members, such as patients, doctors and other medical personnel, associated with the system 10. A multimedia table 172 may be used to store recorded video segments or X-rays or other medical images, and a names/addresses table 174 stores the names and addresses of patients and other members. A notes table 176 may be used to store notes entered into the system by medical personnel, and a patient demographics table 178 may be used to store physical and other characteristics of the patients.

A patient financial table 180 may be used to store patient billing data, and a patient immunizations table 182 may be used to store the immunizations the patient has received. A patient legal table 184 may be used to store references to legal documents relating to the patients, such as living wills, and a patient medications table 186 may be used to store data relating to medications which are administered to patients, including dose and frequency of administration. A patient problems table 188 may be used to store data relating to medical problems of the patients.

A provider profile table 190 may be used to store data relating to the various providers associated with the system 10. A queue table 192 is used to store queue records which, as described below, are used in connection with the transmission of data within the system 10. A security table 194 is used to store passwords of members associated with the system 10. A workstation profile table 196 and a workstation tracking table 198 are used to store data relating to the configuration and operation of the workstations used throughout the system 10.

Figure 9:
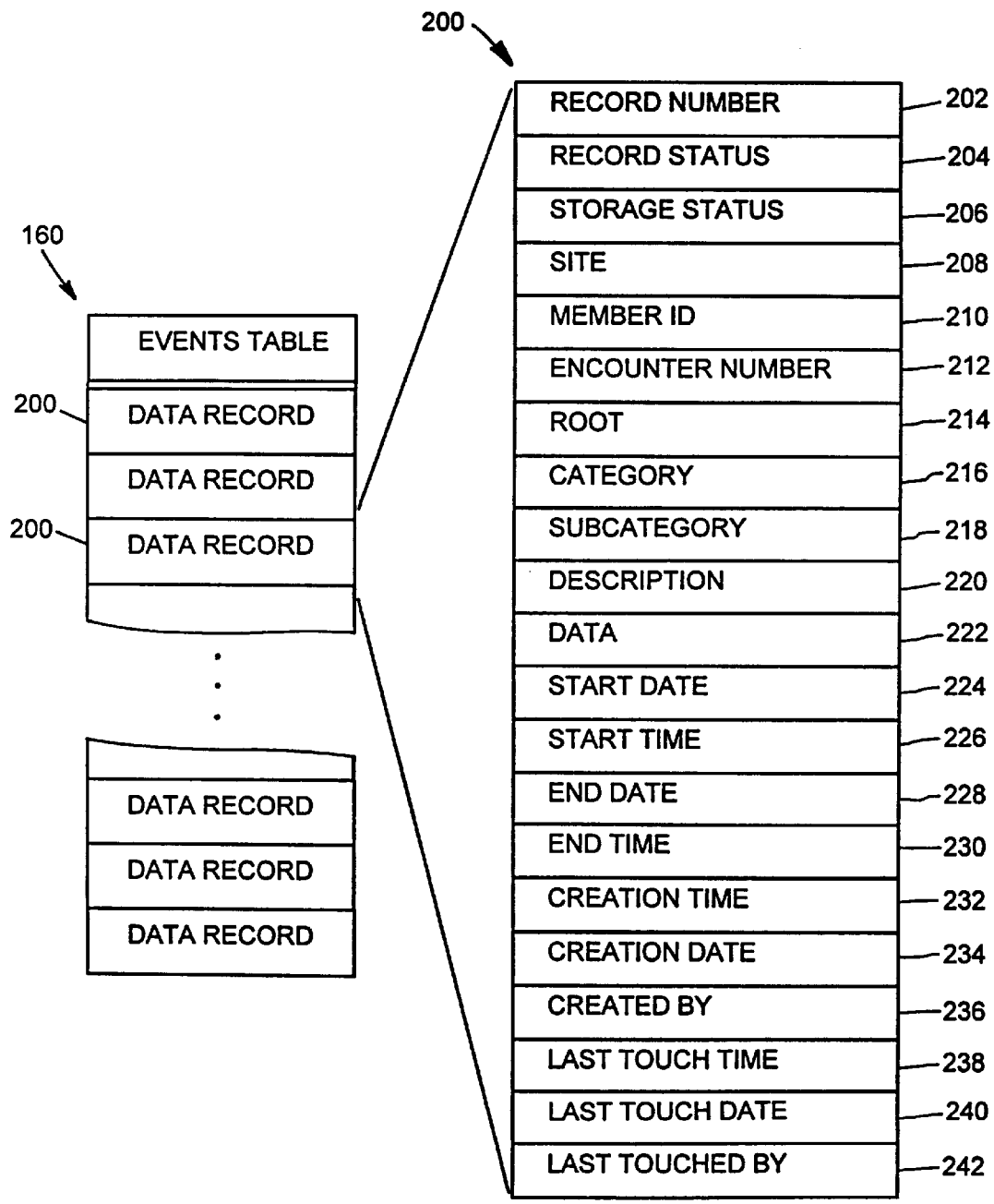
FIG. 9 illustrates the logical organization of the event data table shown schematically in FIG. 8.

FIG. 9 illustrates the individual data records stored in the events table 160 shown schematically in FIG. 8 and a number of data components that are stored in each of those data records. Referring to FIG. 9, the events table 160 includes a number, such as thousands, of individual data records 200. As shown in the right-hand portion of FIG. 9, each data record 200 includes a plurality of data segments, including a first data segment 202 having a record number uniquely identifying the data record 200. The record number may include, for example, a time-related number containing two digits specifying the year, three digits specifying the day of the year (e.g. the 277th day of the year), and a number of digits specifying the exact time at which the record 200 was created (e.g. the number of milliseconds past midnight).

A data segment 204 is used to specify the record status of the data record 200. Possible statuses include unprocessed, processed, exception, clinical, clinical-addressed, administrative, administrative-addressed (a number of these statuses are described below in connection with the operation of the system). A data segment 206 is used to specify the storage status of the data record 200. Possible storage statuses include current, archive and delete. A data segment 208 specifies the site within the system 10 at which the data record 200 was generated, and a data segment 210 specifies a member identification number, such as a patient or doctor, relating to the data record 200. A data segment 212 specifies an encounter number (e.g. a patient's 3rd visit) relating to the data record 200.

Three data segments 214, 216, 218 are used to categorize the data record 200 in a hierarchical manner. The root data segment 214 is used to describe the basic type of data record 200, the category data segment 216 is used to describe one of a number of categories within that particular root, and the subcategory data segment 218 is used to describe one of a number of subcategories within the category specified in the data segment 218.

The root, category and subcategory specified in the segments 214–218 are used to selectively retrieve particular data records 200 from the events table 160. For example, if it were desired to search the events table 160 for the purpose of checking vital signs, the search may be performed by searching for all data records 200 having the root "recording" and the category "vital-signs." All data records 200 having that root and category would be retrieved (via a standard SQL request). If it were desired to search the events table 160 for the purpose of checking all blood pressures, the search may be performed by searching for all data records 200 having the root "recording," the category "vital-signs," and the subcategory "blood-pressure."

A data segment 220 contains a description of the type of data stored in a data segment 222. For example, the description in the segment 220 could be "blood-pressure" and the data in the segment 222 would be the numeric value of the blood pressure. Data segments 224–230 contain time-stamp data relating to action or status represented by the data record 200. Data segments 232–236 store data relating to the creation of the data record 200, and data segments 238–242 store data relating to the latest revision or access of the data record 200.

The data records stored in the other data tables shown schematically in FIG. 8 may have the same or a different organization as that shown in FIG. 9, depending upon the nature of the data stored in the tables. Although a particular data structure has been described in connection with FIGS. 8 and 9, it should be understood that numerous different types of data structures and organizations could be utilized.

Outpatient Data Capture

Outpatient data, such as the data described above in connection with FIGS. 8 and 9, may be captured or entered into the outpatient care system 10 in various ways. As described above, outpatient data may be manually entered by an operator via the data terminals 66 of the metropolitan area data system 14 (FIG. 3), via the workstations 98 of the electronic nursing station 20 (FIG. 4), via the workstation 126 of the skilled care facility system 22 (FIG. 5), via the workstation 146 of the system 24 (FIG. 6), and via the workstation 152 of the system 26 (FIG. 7).

Outpatient data may be automatically entered into the system 10 without the need for human intervention in various ways. Referring to FIG. 5, which illustrates the skilled care facility system 22, clinical patient data may be generated by the patient diagnostic device 132, transmitted to the data center 110, and stored in the memory of the network server 124. Data regarding the operational status of the patient care device 136 may also be generated and stored in a similar manner.

Outpatient data may also be generated at the patient home 18 and transmitted to the metropolitan area data system 14 for storage. This data generation can occur in two ways, either manually by a person at the patient home 18 or automatically from the medical device 29 located at the patient home 18 (the medical device 29 can be either a patient diagnostic device like the device 132 of FIG. 5 or a patient care device like the device 136 of FIG. 5).

Figure 10:
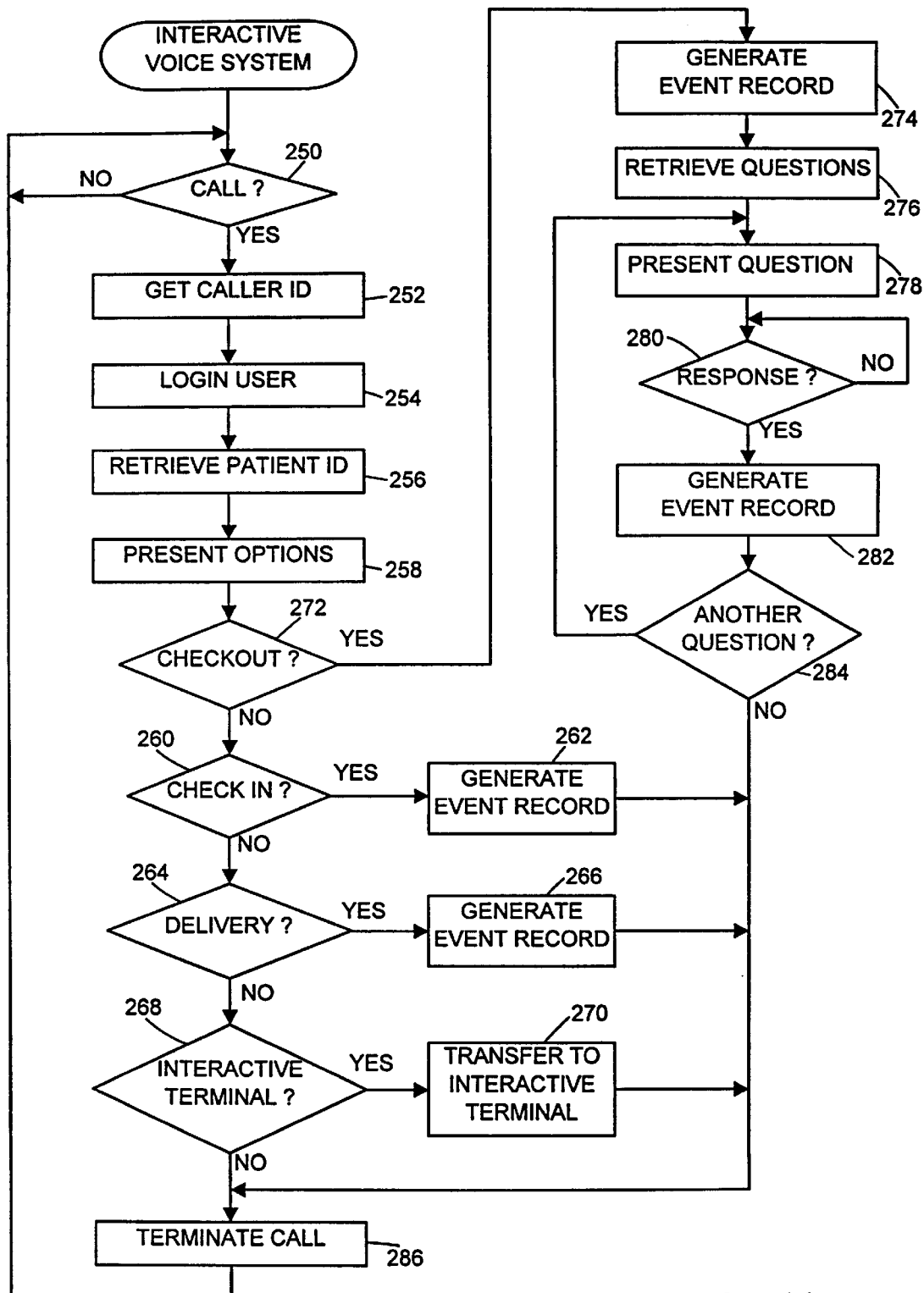
FIG. 10 is a flowchart of a computer program performed by the interactive voice system shown in FIG. 3.

FIG. 10 is a flowchart of a computer program performed by the interactive voice system 70 of the metropolitan area data system 14 (FIG. 3) which facilitates the generation and transmission of outpatient data by a person at the patient home 18 to the metropolitan area data system 14. Referring to FIG. 10, at step 250, the program waits for a telephone call to be placed (the telephone call is initiated by the person at the patient home 18). Upon the initiation of a telephone call, at step 252 the program retrieves the identification of the caller (via a conventional caller-ID feature), in the form of the caller's telephone number. At step 254, the caller is requested to log in, pursuant to which the member ID number of the caller and the caller's password are entered (the password is checked by comparing the entered password with the password stored in the security table 194 (FIG. 8) for that member ID number.

At step 256, the patient identification number is retrieved (by searching the names/addresses table 174 for the telephone number identified at step 252), and at step 258 four options are presented to the caller by a synthesized or recorded voice. The four options include a check-in option, a check-out option, a delivery option, and an interactive terminal option.

Various actions are typically taken at the patient home 18, including the delivery of one or more medical devices and periodic visits to the patient home by medical clinicians to check the status of the patient or administer medical treatment, for example. When such a visit is made, the visiting clinician is required to check in upon arrival at the patient home 18 and check out upon departure from the patient home 18, using the telephone 25 at the patient home 18.

If the caller selects the check-in option as determined at step 260, the program branches to step 262 where an event record is generated to record the time and location (based on the caller ID from step 252) at which the caller checked in. The event record may be provided with the root "recording" and the category "check-in," and the record status is set to "unprocessed" (as described below, the record status of "unprocessed" will trigger a check of the event record by the personnel monitor 86 to determine whether the check-in was timely and at the proper location, after which the record status will be set to "processed" or "administrative").

If the caller selected the delivery option as determined at step 264, the program branches to step 266 where an event record is generated to record the fact that a delivery of a medical device was made. The event record is generated with a root of "recording," a category of "delivery" and a record status of "unprocessed." Data representing the type of medical device delivered (as transmitted by the caller over the telephone line) could also be stored in the event record.

If the caller selected the interactive terminal option as determined at step 268, the program branches to step 270 where the caller is connected to one of the data terminals 66 (FIG. 3).

If the caller selected the check-out option as determined at step 272, the program branches to step 274 where an event record is generated. The event record may be provided with the root "recording," the category "check-out," the record status "unprocessed," and the time and location (based on the caller ID from step 252) of the check-out.

At step 276, the program retrieves a list of questions (which may be stored in the attachments table 162 and which correspond to the patient identification number retrieved at step 256) relating to the patient. Those questions can include questions requesting the caller to input, via the touch tone telephone 25, clinical patient data such as vital signs or subjective data as to how the patient is feeling. At step 278, a question is audibly presented to the caller, and when the caller responds as determined at step 280, the program generates an event record for that patient which contains the information provided by the caller.

After the completion of one of steps 268 or 284, the program branches to step 286 where the telephone call is terminated, and the program branches back to step 250 where it waits for the initiation of the next telephone call.

Figure 11:
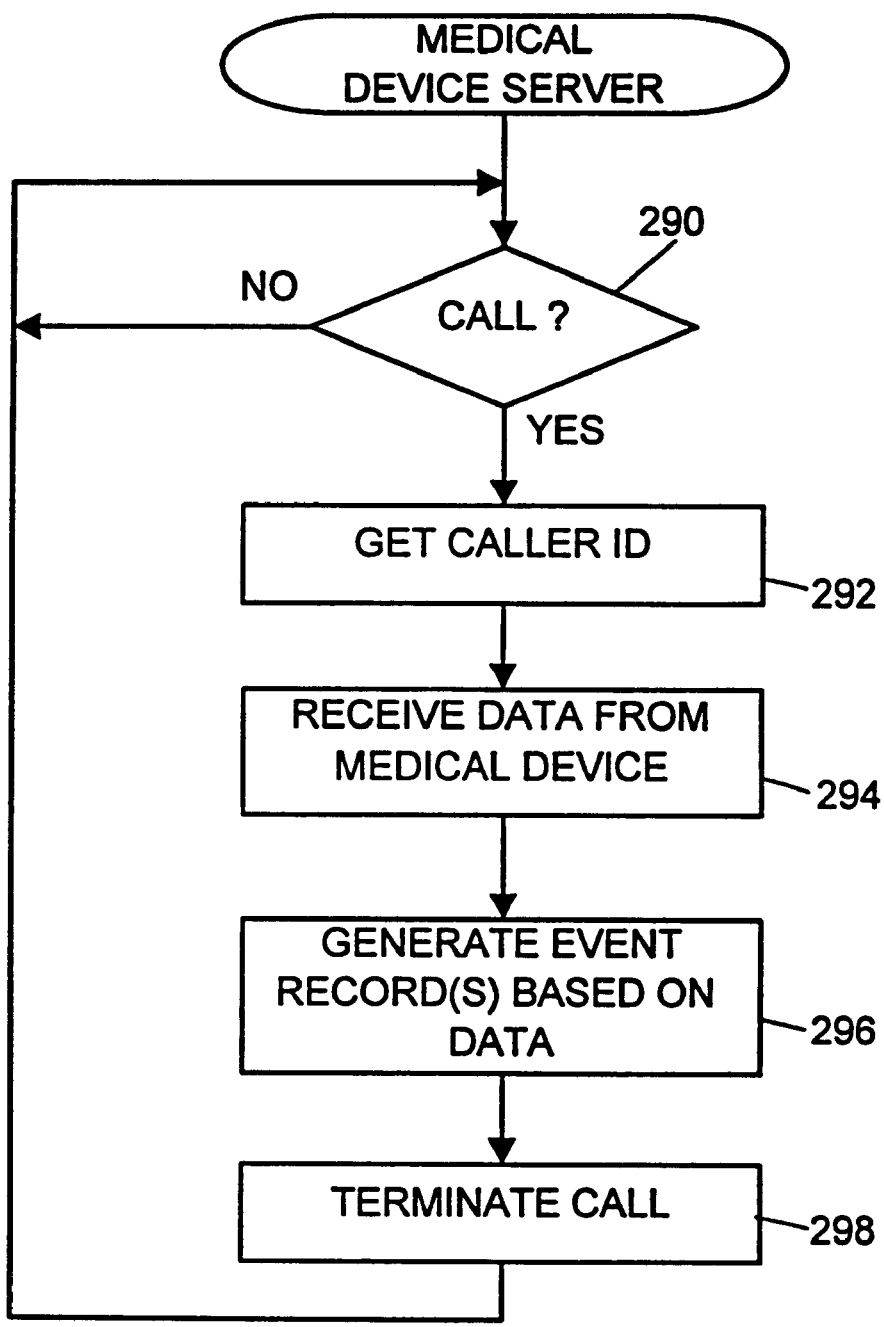
FIG. 11 is a flowchart of a computer program performed by the medical device server shown in FIG. 3.

FIG. 11 is a flowchart of a computer program performed by the medical device server 68 (FIG. 3) to automatically transfer outpatient data from the medical device 29 at the patient home 18 via the modem 30 to the metropolitan area data system 14. The medical device 29 could be programmed to automatically call in on a periodic basis to the metropolitan area data system 14. Referring to FIG. 11, at step 290, the program waits for a telephone call to be placed by the medical device 29. Upon the initiation of a telephone call, at step 292 the program retrieves the identification of the calling location (via a conventional caller-ID feature), in the form of the caller's telephone number. At step 294, the medical device 29 transmits data identifying itself and outpatient data relating to a clinical condition of the patient or to the operational status of the device 29. At step 296, the program generates one or more event records (their record status being set to "unprocessed"), depending on the data that was transmitted by the medical device 29. After the event record(s) are generated, the program branches to step 298 where the call is terminated, and the program branches back to step 290 where it waits for the initiation of the next telephone call.

Monitoring of Outpatient Data

Outpatient data stored in the outpatient care data system 10 is continuously monitored by the monitors 84–92 (FIG. 4) to detect the presence of various conditions. Upon detection of certain conditions, visual messages are selectively displayed on the visual display devices associated with the monitors 84, 86, 88, 92.

Figure 12:
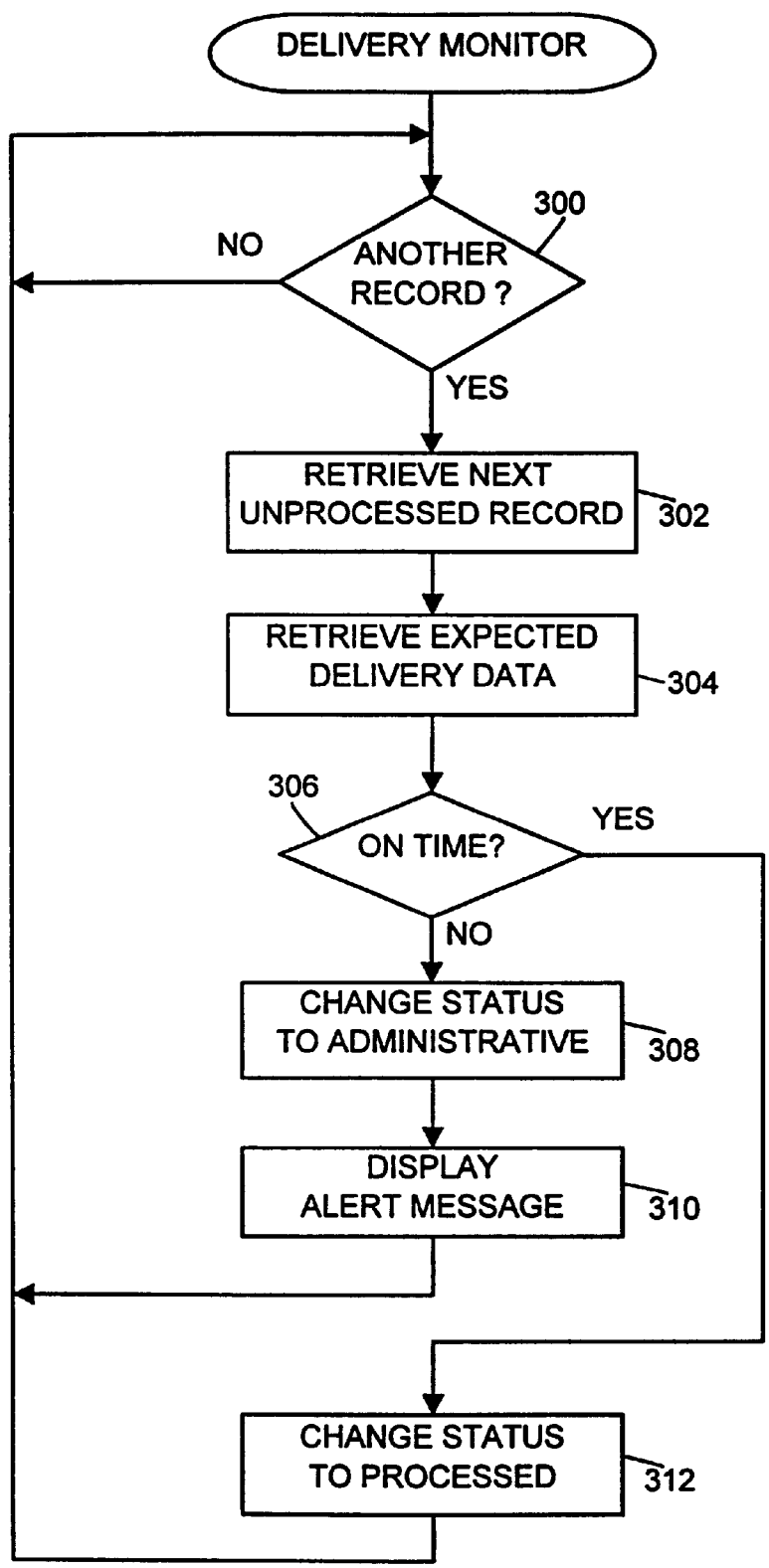
FIG. 12 is a flowchart of a computer program performed by the delivery monitor shown in FIG. 4.

FIG. 12 is a flowchart of a computer program performed by the delivery monitor 84 (FIG. 4). The delivery monitor 84 continuously checks all unprocessed event records corresponding to deliveries of medical devices (which event records were previously generated at step 266 (FIG. 10) of the interactive voice system computer program.

Referring to FIG. 12, at step 300 the program checks whether there are any unprocessed event records corresponding to deliveries of medical devices. This can be determined by searching the events table 160 (FIG. 9) for all data records 200 having a root of "recording," a category of "delivery," and a record status of "unprocessed," which search can be conducted by an SQL search request. If there is such a data record, it is retrieved from the events table 160 at step 302. That data record will have the date and time at which the medical device was actually delivered.

At step 304, the scheduled date and time for the delivery is retrieved by searching for the data record from the attachments table 162 which corresponds to the event record retrieved at step 302. At step 306, if the scheduled date and time for delivery of the medical device do not correspond to the actual date and time of delivery (e.g. on the correct day and within a predetermined period of time, such as 15 minutes), the program branches to step 308, where the record status for the event record is changed from "unprocessed" to "administrative," which status records the fact that the delivery was not made on time. The program then branches to step 310, where an alert message concerning the late or missed delivery is displayed on the display device associated with the delivery monitor 84 (FIG. 4).

If the delivery was made on time as determined at step 306, the program branches to step 312, where the record status of the event record retrieved at step 302 is changed from "unprocessed" to "processed." Consequently, that particular event record will not be checked again by the delivery monitor 84 (FIG. 4).

Figure 13:
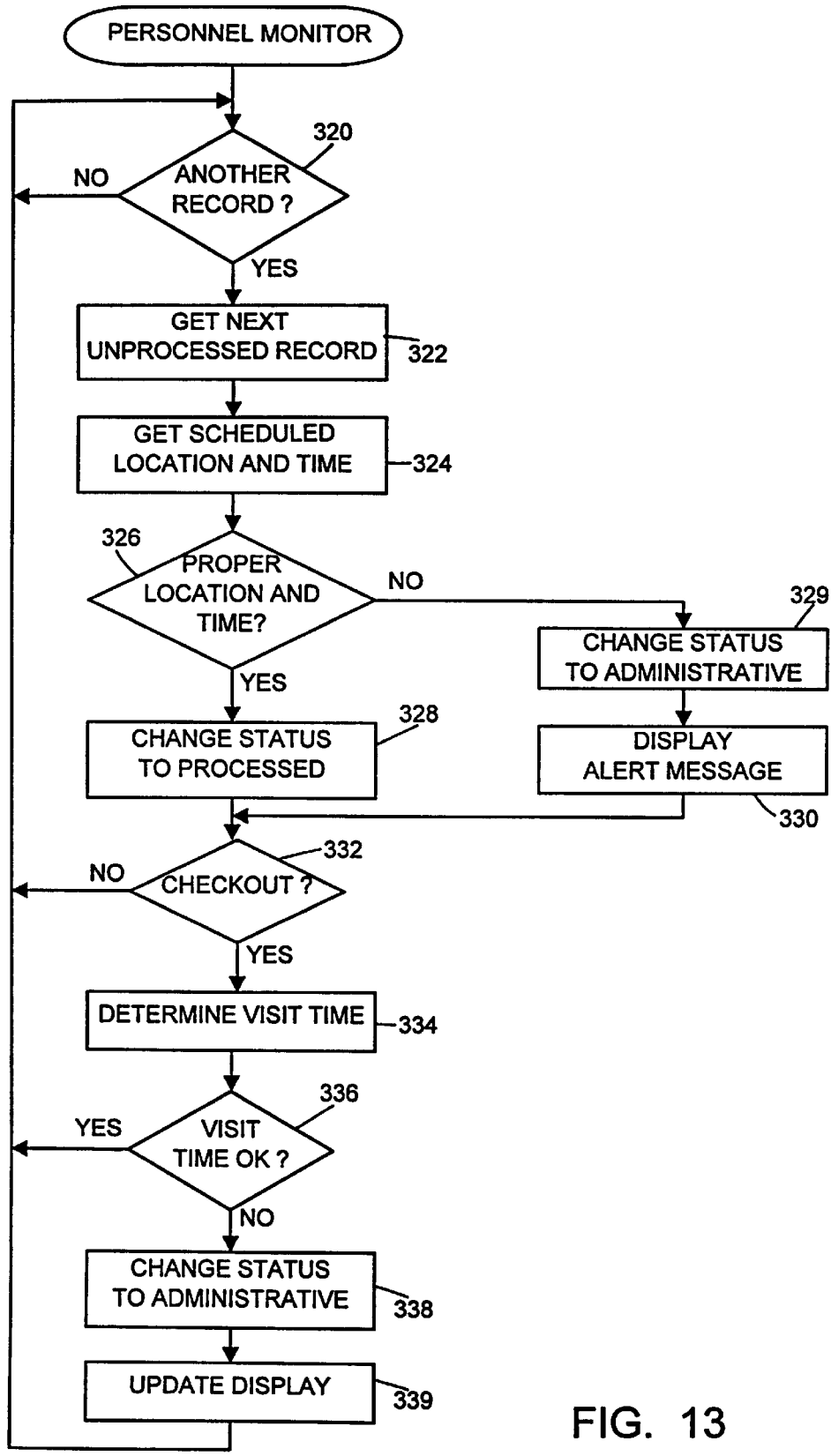
FIG. 13 is a flowchart of a computer program performed by the personnel monitor shown in FIG. 4.

FIG. 13 is a flowchart of a computer program performed by the personnel monitor 86 (FIG. 4). The personnel monitor 86 continuously checks all unprocessed event records corresponding to check-ins and check-outs of medical personnel (which event records were previously generated at steps 262, 274 (FIG. 10) of the interactive voice system computer program.

Referring to FIG. 13, at step 320 the program checks whether there are any unprocessed event records corresponding to check-ins and check-outs of medical personnel. This can be determined by searching the events table 160 (FIG. 9) for all data records 200 having a root of "recording," a category of "check-in" or "check-out," and a record status of "unprocessed." If there is such a data record, it is retrieved from the events table 160 at step 322. That data record will have the date and time at which the check-in or check-out occurred.

At step 324, the scheduled location and time for the check-in or check-out are retrieved by searching for the data record from the attachments table 162 which corresponds to the event record retrieved at step 322. At step 326, if the scheduled location and time corresponds to the actual date and time of the check-in or check-out, the program branches to step 328, where the record status of the event record retrieved at step 322 is changed from "unprocessed" to "processed." Consequently, that particular event record will not be checked again by the personnel monitor 86 (FIG. 4).

If the check-in or check-out was not properly made as determined at step 326, the program branches to step 329, where the record status for the event record is changed from "unprocessed" to "administrative," which status records the fact that the check-in or check-out was not made properly. The program then branches to step 330, where an alert message concerning the improper check-in or check-out is displayed on the visual display of the display device connected to the personnel monitor 86 (FIG. 4).

If the event record retrieved at step 322 corresponded to a check-out, the duration of the visit (the time difference between the check-in and check-out at that location) is checked. At step 332, if the event record retrieved at step 322 does not correspond to a check-out, the program simply returns to step 320. If the event record was a check-out, the program branches to step 334, where the visit time is determined by determining the time difference between the check-out and the previous check-in (having a root of "recording" and a category of "check-in") corresponding to that location. If the visit time is not at least as large as a minimum visit time, e.g. fifteen minutes, as determined at step 336, the program branches to step 338 where the record status of the event record retrieved at step 322 is changed to "administrative" and to step 339 where the display of the display device for the personnel monitor 86 (FIG. 4) is updated to indicate that the visit was too short.

Figure 14:
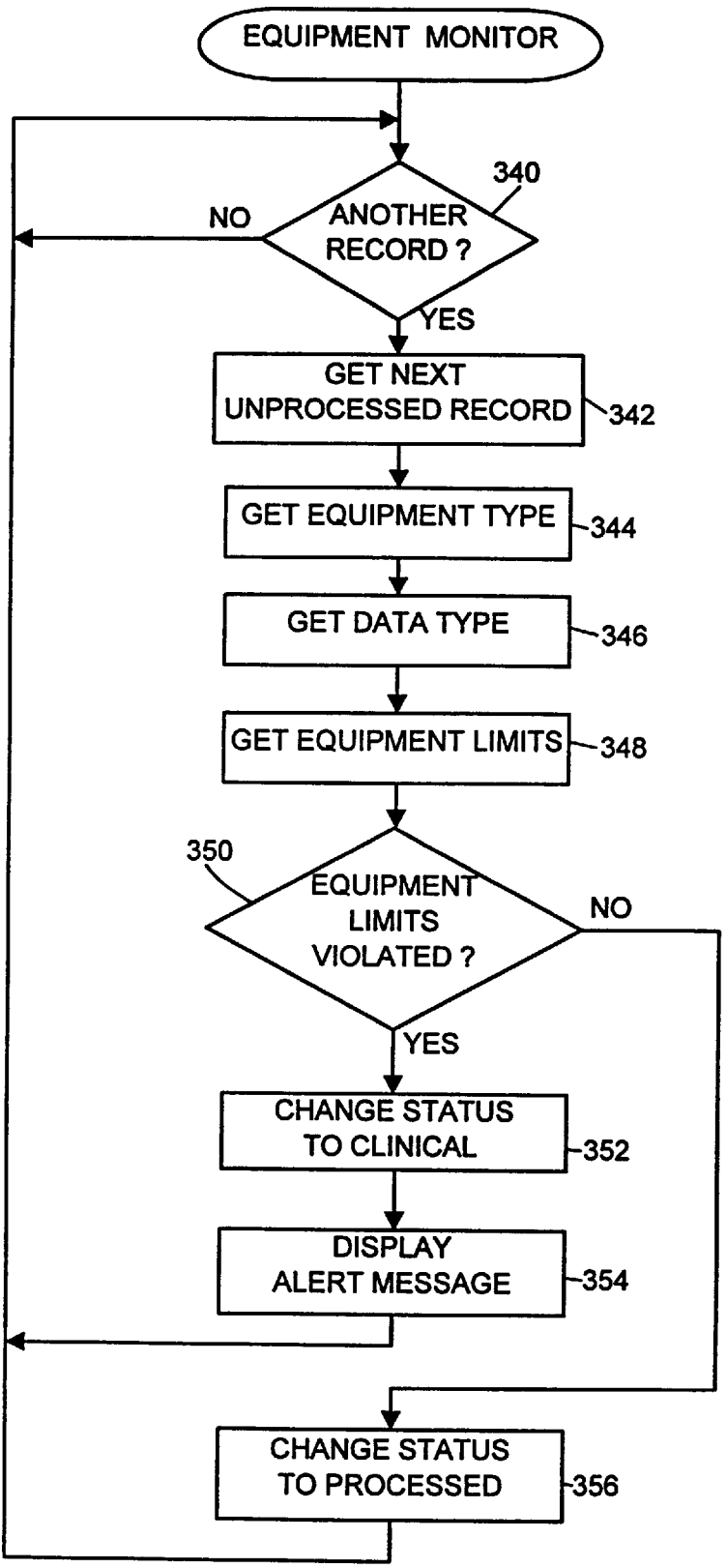
FIG. 14 is a flowchart of a computer program performed by the equipment monitor shown in FIG. 4.

FIG. 14 is a flowchart of a computer program performed by the equipment monitor 88 (FIG. 4). The equipment monitor 88 continuously checks all unprocessed event records which store data relating to the operational status of medical devices within the system 10. Referring to FIG. 14, at step 340 the program checks whether there are any unprocessed event records corresponding to equipment operational status. If there is such a data record, it is retrieved from the events table 160 at step 342. At steps 344 and 346, the particular type of medical device and data transmitted by the medical device are determined from data stored in the event record. The data transmitted by the device may be, for example, pressure data or voltage data. At step 348, the equipment limits for that particular type of medical device and data type are retrieved from the corresponding data record in the attachments table 162.

At step 350, if the equipment limits retrieved at step 348 are exceeded by the data transmitted by the medical device and stored in the data record retrieved at step 342, the program branches to step 352 where the record status of the data record retrieved at step 342 is set to "clinical" to signify a problem with the operational status of the medical device (e.g. a low battery voltage), and the program branches to step 354 where a corresponding alert message is displayed on the display device associated with the equipment monitor 88.

Figure 15:
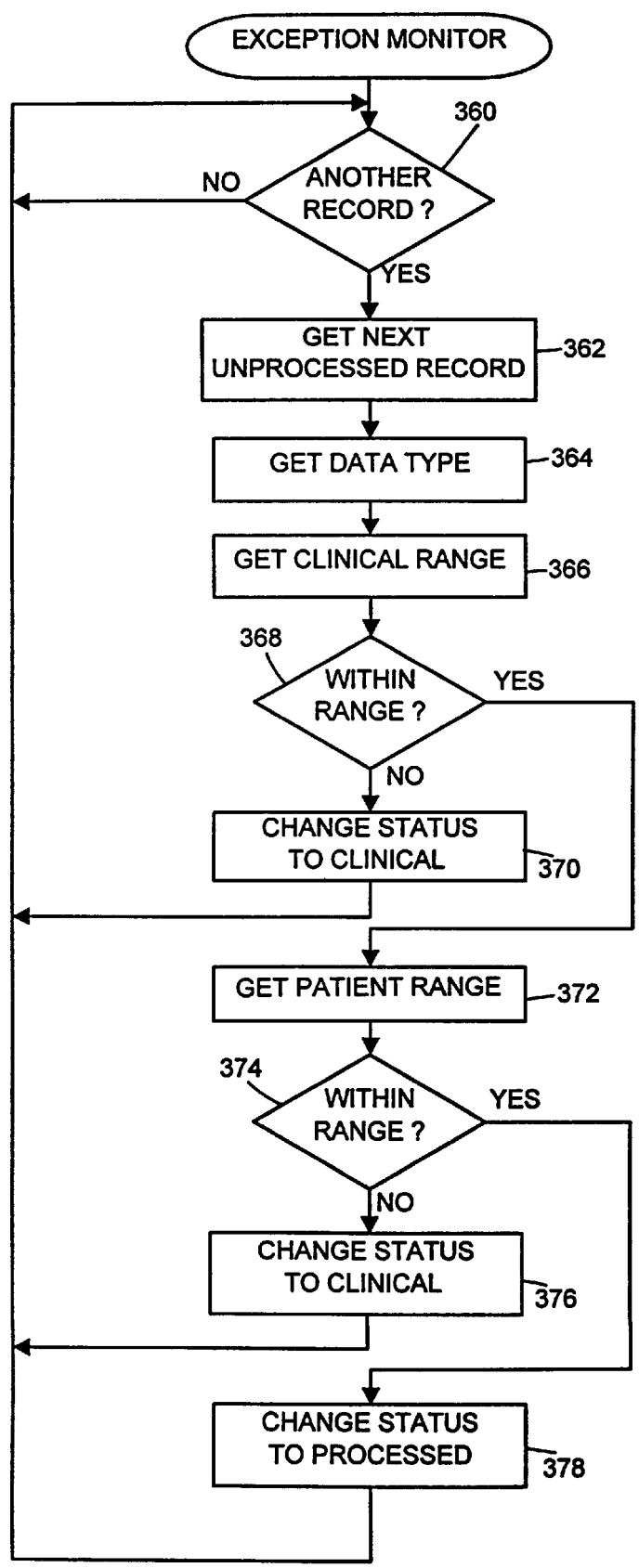
FIG. 15 is a flowchart of a computer program performed by the exception monitor shown in FIG. 4.

FIG. 15 is a flowchart of a computer program performed by the exception monitor 90 (FIG. 4). The exception monitor 90 continuously checks all unprocessed event records which store clinical outpatient data, such as vital signs, which may indicate the existence of an emergency medical condition or a medical condition that needs attention. Referring to FIG. 15, at step 360 the program checks whether there are any unprocessed event records corresponding to clinical conditions. This may be performed by searching the events table 160 for event records having a root of "recording," a category of "vital-signs" and a record status of "unprocessed."

If there is such a data record, it is retrieved from the events table 160 at step 362. At step 364, the data type is retrieved from the event record by checking the its subcategory, which may be "temperature" for example. At step 366, the clinical range for that subcategory is retrieved from a corresponding data record in the attachments table 162. For example, where the data type is temperature, the clinical range might be 90° to 110°, meaning that the patient's temperature should fall within the clinical range.

At step 368, the clinical data for the patient stored in the event record retrieved at step 362 is compared to determine whether it falls within the clinical range limits retrieved at step 366. If not, the program branches to step 370 where the record status of the event record is changed to "clinical," and the program branches back to step 360.

If the clinical data falls within the clinical range as determined at step 368, the program branches to step 372, where the patient range is retrieved from a corresponding data record in the attachments table 162. For example, where the data type is temperature, the patient range might be 96° to 104°. At step 374, the clinical data for the patient stored in the event record retrieved at step 362 is compared to determine whether it falls within the patient range limits retrieved at step 372. If not, the program branches to step 376 where the record status of the event record is changed to "clinical," and the program branches back to step 360. If the clinical data is within the patient range, the program branches to step 378 where the record status of the event record retrieved at step 362 is set to "processed."

Figure 16:
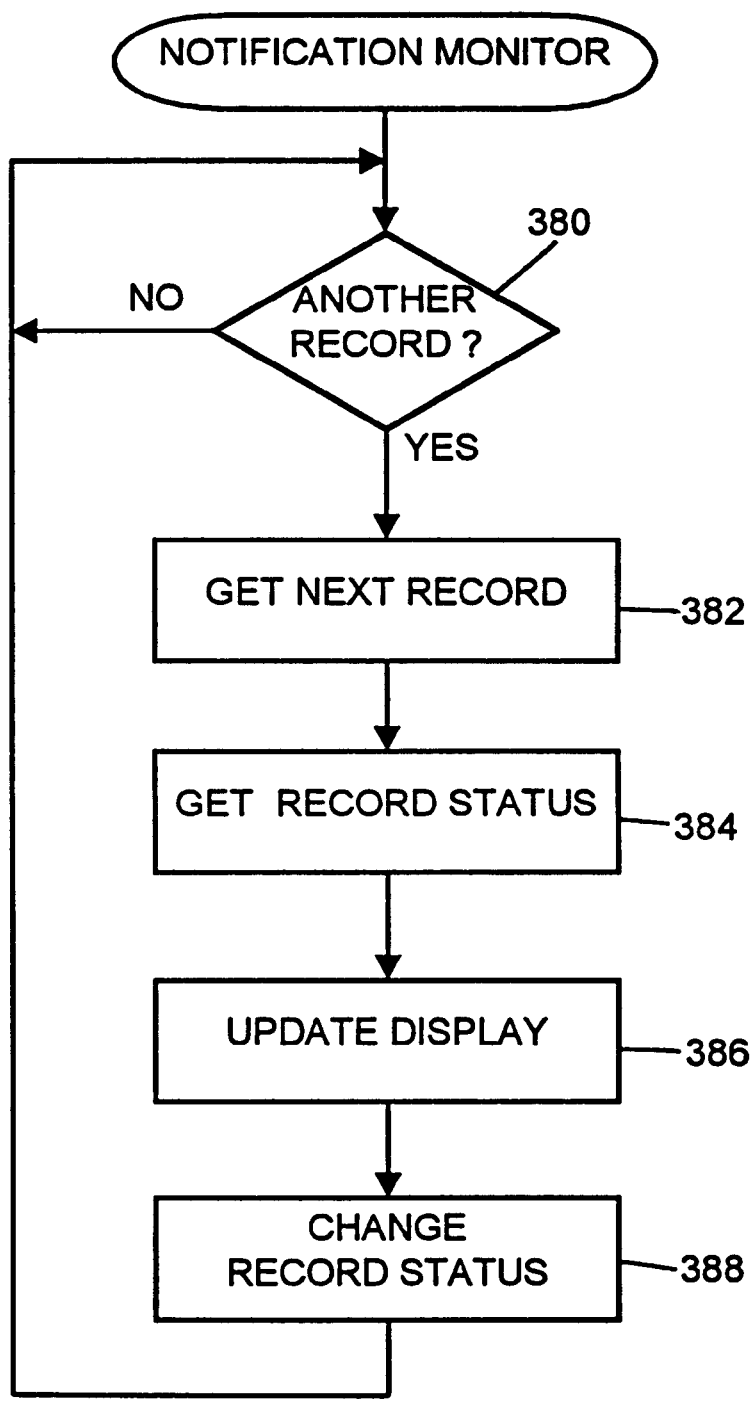
FIG. 16 is a flowchart of a computer program performed by the notification monitor shown in FIG. 4.

FIG. 16 is a flowchart of a computer program performed by the notification monitor 92 (FIG. 4). The notification monitor 92 continuously checks all event records to locate any event record having clinical outpatient data, such as vital signs, which have a record status of "clinical" (which indicates the existence of an emergency medical condition or a medical condition that needs attention) and any event record having a message intended for a physician (e.g. an event record having a root of "recording," a category of "doctor," a subcategory of "notification" and a record status of "unprocessed"). The monitor 92 could also search for other event records which are desired to be brought to the attention of a physician. In response to finding such event records, the notification monitor 92 causes an appropriate message to be displayed on the display device associated with the notification monitor 92, which display is provided for review by physicians or other medical personnel at the hospital at which the monitor 92 is located.

Referring to FIG. 16, at step 380, the program searches for the existence of an event record of the type described above, and gets the next such record at step 382. At step 384, the record status of the event record is retrieved. Based on the record status, the display is updated at step 386. For example, for a clinical condition, the message could be in the form of the corresponding physician's name in red, and for a non-clinical condition, e.g. a note to a physician, the message could be in the form of the physician's name in yellow. At step 388, the record status of the event record retrieved at step 382 is changed. For example, for an event record having clinical data, the record status could be changed from "clinical" to "clinical-addressed." For an event record containing a note to a physician, the record status could be changed from "unprocessed" to "processed."

Transmission of Outpatient Data Within System

Figure 17:
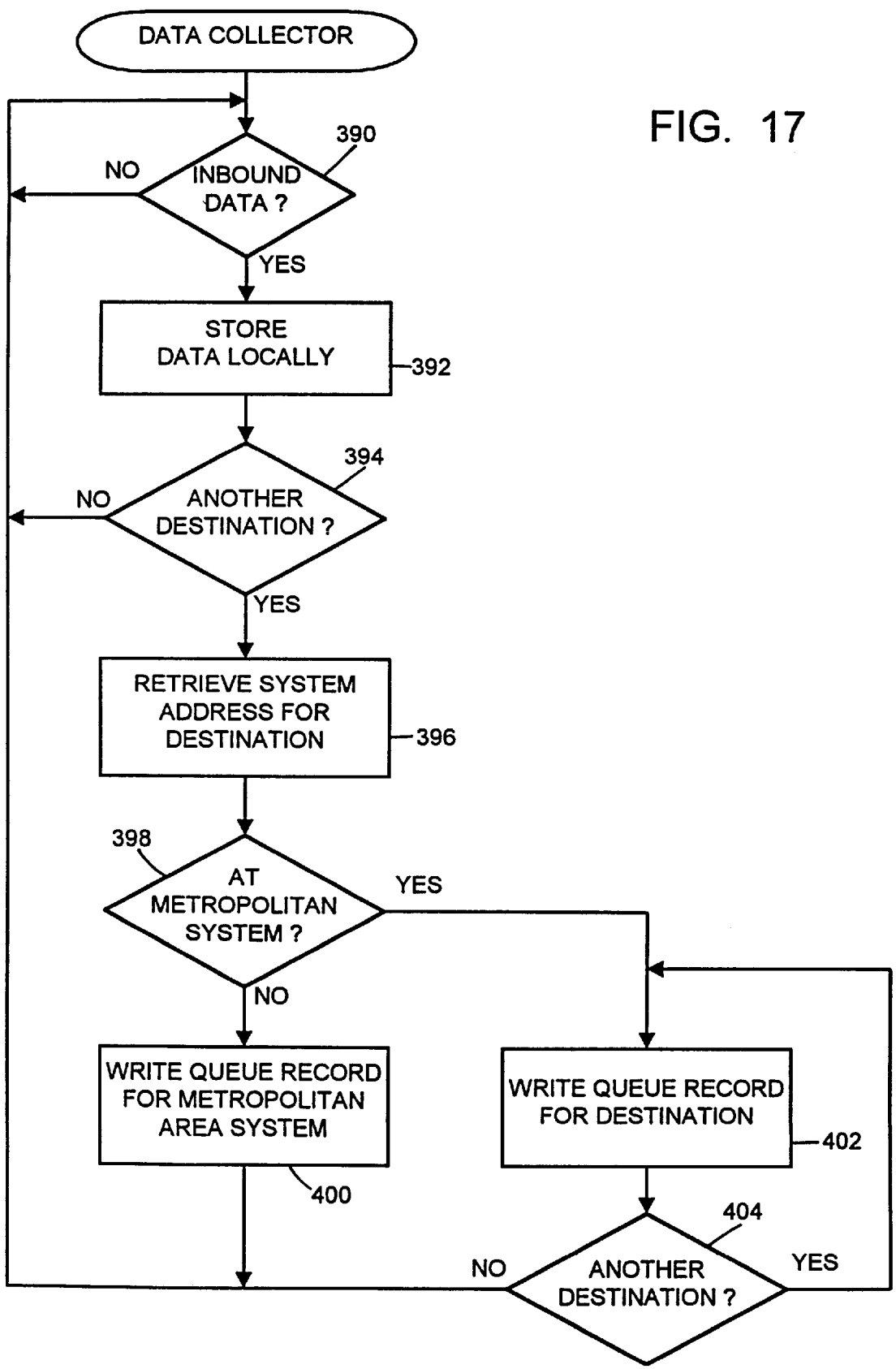
FIG. 17 is a flowchart of a computer program performed by each of the data collectors shown in FIGS. 2 and 3.

FIG. 17 is a flowchart of a computer program performed by each of the data collectors 38, 58 shown in FIGS. 2 and 3. Each of the data collectors 38, 58 responds to inbound data on a real-time basis, stores the data locally, and determines whether the inbound data needs to be transmitted to another location. If so, the data collectors 38, 58 cause the inbound data to be transmitted (by the data transporters 36, 56) to each intended location.

Referring to FIG. 17, at step 390, if there is an inbound data record, the program branches to step 392, where the inbound data record is stored at the location at which the data collector 38 or 58 is situated. For example, in the case of the data collector 38, the inbound data record is stored in the data storage unit 44 (FIG. 2). At step 394, the program determines whether the inbound data record needs to be transmitted to another destination. This step may be accomplished by determining the patient identification number from the inbound data record, and checking the central reference table 164 (FIG. 8) to determine the list of all parties (referred to as members in data segment 210 shown in FIG. 9) interested in receiving data regarding that particular patient.

If there is another destination, the program branches to step 396 where the system address for the destination is retrieved from the system addresses table 166 (which cross references each member identification number with its corresponding system address). At step 398, if the data collector 38 or 58 is located at the metropolitan area data system 14, the program branches to steps 402–404, where it writes a queue record for each destination to which the data record needs to be sent. Each queue record written at step 404 contains the contents of the inbound data record and the system address for one of the intended destinations. The queue records are stored locally in memory, and as described below, the data transporters 36, 56 cause the data records specified by the queue records to be transmitted to their intended destinations.

If the data collector 38 or 58 is not located at the metropolitan area data system 14 as determined at step 398, the program branches to step 400, where it writes and locally stores a queue record containing the contents of the inbound data record and the system address for the metropolitan area data system 14 to which the patient is assigned.

Figure 18:
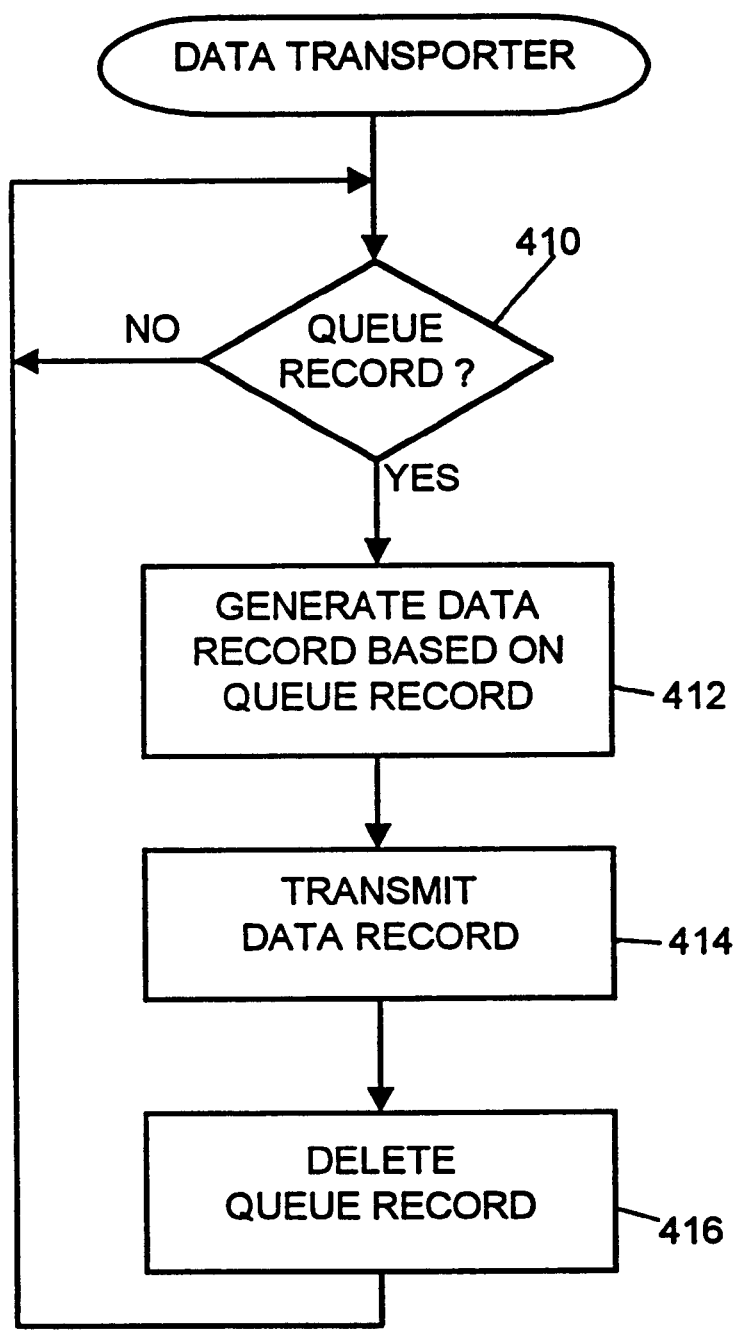
FIG. 18 is a flowchart of a computer program performed by each of the data transporters shown in FIGS. 2 and 3.

FIG. 18 is a flowchart of a computer program performed by each of the data transporters 36, 56 shown in FIGS. 2 and 3. The data transporters 36, 56 transmit data records to various locations within the system based on the queue records described above in connection with FIG. 17. Referring to FIG. 18, if there is another stored queue record as determined at step 410, the program branches to step 412, where a data record corresponding to the queue record is generated. At step 414, the data record is transmitted to the system address set forth in the queue record, and at step 416 the queue record is deleted from memory.

Numerous modifications and alternative embodiments of the invention will be apparent to those skilled in the art in view of the foregoing description. This description is to be construed as illustrative only, and is for the purpose of teaching those skilled in the art the best mode of carrying out the invention. The details of the structure and method may be varied substantially without departing from the spirit of the invention, and the exclusive use of all modifications which come within the scope of the appended claims is reserved.

What is claimed is:

1. An outpatient care data system, comprising:

a data storage system located at a hospital and which stores outpatient data in the form of a plurality of medical records for a plurality of outpatients associated with said outpatient care data system, said medical records including, for each outpatient, an identification of the outpatient and data relating to the medical history of the outpatient;

a data receiver coupled to said data storage system, said data receiver being adapted to receive outpatient data from a first outpatient system situated at a first location remote from said hospital and being adapted to receive outpatient data from a second outpatient system situated at a second location remote from said hospital; and a monitor for checking outpatient data stored in said data storage system and generating messages relating to said outpatients, said monitor being programmed to determine whether a deliverable medical device was delivered to an outpatient home in accordance with a scheduled delivery time and to generate a message relating to whether said deliverable medical device was delivered in accordance with said scheduled delivery time.

2. A system as defined in claim 1 additionally comprising a data transmitter coupled to said data storage system, said data transmitter being adapted to transmit data from said medical records to a plurality of interactive computer terminals disposed at different terminal locations on a real-time basis.

3. A system as defined in claim 1 additionally comprising:

a first outpatient system operatively coupled to said data storage system on a real-time basis, said first outpatient system being situated at a first location remote from said hospital, said first remote location being a non-hospital location, said first outpatient system including a medical device associated with an outpatient present at said first remote location; and a second outpatient system operatively coupled to said data storage system on a real-time basis, said second outpatient system being situated at a second location remote from said hospital, said second remote location being a non-hospital location, said second outpatient system including a medical device associated with an outpatient present at said second remote location.

4. A system as defined in claim 3 wherein said first outpatient system is a skilled care facility system comprising:

at least one medical device for administering medical treatment to an outpatient at said first remote location;

at least one medical device for sensing a medical condition of an outpatient at said first remote location and generating outpatient condition data relating to said medical condition; and a transmitter that transmits said outpatient condition data from said first remote location to said data storage system on a real-time basis.

5. A system as defined in claim 3 wherein said second outpatient system comprises:

at least one medical device located at an outpatient home; and a transmitter that transmits outpatient data from said outpatient home to said data storage system on a real-time basis.

6. A system as defined in claim 1 additionally comprising a monitor programmed to compare outpatient data representing a clinical condition of an outpatient with a predetermined limit and to generate a message relating to whether said outpatient data is within said predetermined limit.

7. An outpatient care data system, comprising:

a data storage system located at a hospital and which stores outpatient data in the form of a plurality of medical records for a plurality of outpatients associated with said outpatient care data system, said medical records including, for each outpatient, an identification of the outpatient and data relating to the medical history of the outpatient;

a data receiver coupled to said data storage system, said data receiver being adapted to receive outpatient data from a first outpatient system situated at a first location remote from said hospital and being adapted to receive outpatient data from a second outpatient system situated at a second location remote from said hospital; and a monitor for checking outpatient data stored in said data storage system and generating messages relating to said outpatients, said monitor being programmed to determine whether a medical clinician checked into an outpatient home in accordance with a scheduled check-in time and to generate a message relating to whether said medical clinician checked in in accordance with said scheduled check-in time.

8. A system as defined in claim 7 additionally comprising a data transmitter coupled to said data storage system, said data transmitter being adapted to transmit data from said medical records to a plurality of interactive computer terminals disposed at different terminal locations on a real-time basis.

9. A system as defined in claim 7 additionally comprising:

a first outpatient system operatively coupled to said data storage system on a real-time basis, said first outpatient system being situated at a first location remote from said hospital, said first remote location being a non-hospital location, said first outpatient system including a medical device associated with an outpatient present at said first remote location; and a second outpatient system operatively coupled to said data storage system on a real-time basis, said second outpatient system being situated at a second location remote from said hospital, said second remote location being a non-hospital location, said second outpatient system including a medical device associated with an outpatient present at said second remote location.

10. A system as defined in claim 9 wherein said first outpatient system is a skilled care facility system comprising:

at least one medical device for administering medical treatment to an outpatient at said first remote location;

at least one medical device for sensing a medical condition of an outpatient at said first remote location and generating outpatient condition data relating to said medical condition; and a transmitter that transmits said outpatient condition data from said first remote location to said data storage system on a real-time basis.

11. A system as defined in claim 9 wherein said second outpatient system comprises:

at least one medical device located at an outpatient home; and a transmitter that transmits outpatient data from said outpatient home to said data storage system on a real-time basis.

12. A system as defined in claim 7 additionally comprising a monitor programmed to compare outpatient data representing a clinical condition of an outpatient with a predetermined limit and to generate a message relating to whether said outpatient data is within said predetermined limit.

13. An outpatient care data system, comprising:

a data storage system located at a hospital and which stores outpatient data in the form of a plurality of medical records for a plurality of outpatients associated with said outpatient care data system, said medical records including, for each outpatient, an identification of the outpatient and data relating to the medical history of the outpatient;

a data receiver coupled to said data storage system, said data receiver being adapted to receive outpatient data from a first outpatient system situated at a first location remote from said hospital and being adapted to receive outpatient data from a second outpatient system situated at a second location remote from said hospital; and a monitor for checking outpatient data stored in said data storage system and generating messages relating to said outpatients, said monitor being programmed to determine whether a medical clinician checked out of an outpatient home in accordance with a scheduled check-out time and to generate a message relating to whether said medical clinician checked out in accordance with said scheduled check-out time.

14. A system as defined in claim 13 additionally comprising a data transmitter coupled to said data storage system, said data transmitter being adapted to transmit data from said medical records to a plurality of interactive computer terminals disposed at different terminal locations on a real-time basis.

15. A system as defined in claim 13 additionally comprising:

a first outpatient system operatively coupled to said data storage system on a real-time basis, said first outpatient system being situated at a first location remote from said hospital, said first remote location being a non-hospital location, said first outpatient system including a medical device associated with an outpatient present at said first remote location; and a second outpatient system operatively coupled to said data storage system on a real-time basis, said second outpatient system being situated at a second location remote from said hospital, said second remote location being a non-hospital location, said second outpatient system including a medical device associated with an outpatient present at said second remote location.

16. A system as defined in claim 15 wherein said first outpatient system is a skilled care facility system comprising:

at least one medical device for administering medical treatment to an outpatient at said first remote location;

at least one medical device for sensing a medical condition of an outpatient at said first remote location and generating outpatient condition data relating to said medical condition; and a transmitter that transmits said outpatient condition data from said first remote location to said data storage system on a real-time basis.

17. A system as defined in claim 15 wherein said second outpatient system comprises:

at least one medical device located at an outpatient home; and a transmitter that transmits outpatient data from said outpatient home to said data storage system on a real-time basis.

18. A system as defined in claim 13 additionally comprising a monitor programmed to compare outpatient data representing a clinical condition of an outpatient with a predetermined limit and to generate a message relating to whether said outpatient data is within said predetermined limit.

19. An outpatient care data system, comprising:

a data storage system located at a hospital and which stores outpatient data in the form of a plurality of medical records for a plurality of outpatients associated with said outpatient care data system, said medical records including, for each outpatient, an identification of the outpatient and data relating to the medical history of the outpatient;

a data receiver coupled to said data storage system, said data receiver being adapted to receive outpatient data from a first outpatient system situated at a first location remote from said hospital and being adapted to receive outpatient data from a second outpatient system situated at a second location remote from said hospital; and a monitor for checking outpatient data stored in said data storage system and generating messages relating to said outpatients, said monitor being programmed to determine the duration of a visit of a medical clinician to an outpatient home and to generate a message relating to whether said duration of said visit exceeded a minimum time.

20. A system as defined in claim 19 additionally comprising a data transmitter coupled to said data storage system, said data transmitter being adapted to transmit data from said medical records to a plurality of interactive computer terminals disposed at different terminal locations on a real-time basis.

21. A system as defined in claim 19 additionally comprising:
- a first outpatient system operatively coupled to said data storage system on a real-time basis, said first outpatient system being situated at a first location remote from said hospital, said first remote location being a non-hospital location, said first outpatient system including a medical device associated with an outpatient present at said first remote location; and
- a second outpatient system operatively coupled to said data storage system on a real-time basis, said second outpatient system being situated at a second location remote from said hospital, said second remote location being a non-hospital location, said second outpatient system including a medical device associated with an outpatient present at said second remote location.

22. A system as defined in claim 21 wherein said first outpatient system is a skilled care facility system comprising:
- at least one medical device for administering medical treatment to an outpatient at said first remote location;
- at least one medical device for sensing a medical condition of an outpatient at said first remote location and generating outpatient condition data relating to said medical condition; and
- a transmitter that transmits said outpatient condition data from said first remote location to said data storage system on a real-time basis.

23. A system as defined in claim 21 wherein said second outpatient system comprises:
- at least one medical device located at an outpatient home; and
- a transmitter that transmits outpatient data from said outpatient home to said data storage system on a real-time basis.

24. A system as defined in claim 19 additionally comprising a monitor programmed to compare outpatient data representing a clinical condition of an outpatient with a predetermined limit and to generate a message relating to whether said outpatient data is within said predetermined limit.

25. An outpatient care data system dedicated to the transmission, storage, collection, distribution and retrieval of outpatient data relating to care of outpatients, said outpatient care data system comprising:
- a regional data system for a regional area, said regional data system storing outpatient data in the form of a plurality of comprehensive medical records for a plurality of outpatients located within said regional area, said medical records including, for each regional area outpatient, an identification of the regional area outpatient, the address of the regional area outpatient, an identification of the regional area outpatient's physician, and data representing the medical history of the regional area outpatient;
- a first metropolitan area data system operatively connected to said regional data system, said first metropolitan area data system being associated with a first metropolitan area, said first metropolitan area data system storing outpatient data in the form of a plurality of comprehensive medical records for a plurality of outpatients located within said first metropolitan area, said medical records including, for each first metropolitan area outpatient, an identification of the first metropolitan area outpatient, the address of the first metropolitan area outpatient, and data representing the medical history of the first metropolitan area outpatient, said first metropolitan area data system comprising:
  - a first electronic nursing station located within a first hospital;
  - a first outpatient system operatively coupled to said first electronic nursing station on a real-time basis, said first outpatient system being situated at a first location remote from said first hospital, said first remote location being a non-hospital location, said first outpatient system including a medical device associated with an outpatient present at said first remote location;
  - a second outpatient system operatively coupled to said first electronic nursing station on a real-time basis, said second outpatient system being situated at a second location remote from said first hospital, said second remote location being a non-hospital location, said second outpatient system including a medical device associated with an outpatient present at said second remote location;
  - a second electronic nursing station located within a second hospital, said second hospital being different than said first hospital;
  - a third outpatient system operatively coupled to said second electronic nursing station on a real-time basis, said third outpatient system being situated at a third location remote from said second hospital, said third remote location being a non-hospital location, said third outpatient system including a medical device associated with an outpatient present at said third remote location;
  - a fourth outpatient system operatively coupled to said second electronic nursing station on a real-time basis, said fourth outpatient system being situated at a fourth location remote from said second hospital, said fourth remote location being a non-hospital location, said fourth outpatient system including a medical device associated with an outpatient present at said fourth remote location; and
  - a plurality of interactive computer terminals disposed at different terminal locations remote from said first and second hospitals at which said first and second electronic nursing stations are located, said interactive computer terminals facilitating real-time retrieval at said remote terminal locations of data in said comprehensive medical records for said outpatients located in the first metropolitan area associated with said first metropolitan area data system;
- a second metropolitan area data system operatively connected to said regional data system, said second metropolitan area data system being associated with a second metropolitan area, said second metropolitan area data system storing outpatient data in the form of a plurality of comprehensive medical records for a plurality of outpatients located within said second metropolitan area, said medical records including, for each second metropolitan area outpatient, an identification of the second metropolitan area outpatient, the address of the second metropolitan area outpatient, and data representing the medical history of the second metropolitan area outpatient.

26. A system as defined in claim 25 wherein said first outpatient system is a skilled care facility system comprising:

at least one medical device for administering medical treatment to an outpatient at said first remote location;

at least one medical device for sensing a medical condition of an outpatient at said first remote location and generating outpatient condition data relating to said medical condition; and means for transmitting said outpatient condition data from said first remote location to said electronic nursing station on a real-time basis.

27. A system as defined in claim 25 wherein said second outpatient system is located at an outpatient home.

28. A system as defined in claim 27 wherein said second outpatient system comprises:

at least one medical device located at said outpatient home; and means for transmitting outpatient data from said outpatient home to said electronic nursing station on a real-time basis.

29. A system as defined in claim 28 wherein said means for transmitting outpatient data from said outpatient home to said electronic nursing station comprises a touch-tone telephone.

\* \* \* \* \*